US008679494B2

(12) United States Patent
Ceska et al.

(10) Patent No.: US 8,679,494 B2
(45) Date of Patent: *Mar. 25, 2014

(54) ANTIBODIES SPECIFIC TO IL-17A AND IL-17F

(75) Inventors: Thomas Allen Ceska, Slough (GB); Alistair James Henry, Slough (GB)

(73) Assignee: UCB Pharma S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/989,373

(22) PCT Filed: Apr. 22, 2009

(86) PCT No.: PCT/GB2009/001026
§ 371 (c)(1),
(2), (4) Date: Jan. 26, 2011

(87) PCT Pub. No.: WO2009/130459
PCT Pub. Date: Oct. 29, 2009

(65) Prior Publication Data
US 2011/0262443 A1    Oct. 27, 2011

(30) Foreign Application Priority Data
Apr. 23, 2008 (GB) .................................. 0807413.0

(51) Int. Cl.
*A61K 39/395* (2006.01)
(52) U.S. Cl.
USPC .................. 424/133.1; 424/145.1; 530/387.3; 530/388.23; 530/351
(58) Field of Classification Search
None
See application file for complete search history.

(56) References Cited

U.S. PATENT DOCUMENTS

| 8,303,953 B2 * | 11/2012 | Adams et al. ............. 424/133.1 |
| 2007/0009959 A1 | 1/2007 | Lawson et al. |
| 2007/0160576 A1 * | 7/2007 | Arnott et al. .................. 424/85.2 |
| 2008/0044423 A1 | 2/2008 | Cochrane et al. |
| 2008/0181888 A1 | 7/2008 | Ambrose et al. |

FOREIGN PATENT DOCUMENTS

| WO | WO 00/69463 A1 | 11/2000 |
| WO | 2004106377 | 12/2004 |
| WO | WO 2004/16377 A1 | 12/2004 |
| WO | WO 2005/010044 A2 | 2/2005 |
| WO | 2005051422 | 6/2005 |
| WO | 2006013107 | 2/2006 |
| WO | WO 2006/054059 A1 | 5/2006 |
| WO | WO 2006/088833 A2 | 8/2006 |
| WO | 2007070750 | 6/2007 |
| WO | 2007106769 | 9/2007 |
| WO | 2007149032 | 12/2007 |
| WO | 2008001063 | 1/2008 |
| WO | 2008021156 | 2/2008 |
| WO | 2008047134 | 4/2008 |

OTHER PUBLICATIONS

PCT International Search Report of PCT International Application PCT/GB2009/001026, filed Apr. 22, 2009.
Anti-human IL-17 Antibody, R& D Systems, Aug. 28, 2007, retrieved from internet: http://www.mdsystems, com/pdf/ af317na.pdf on Mar. 27, 2008.
Boder, et al., "Direct evolution of antibody fragments with monvalent femtomolar antigen-binding affinity", Proceedings of the National Academy of Sciences of USA, vol. 97, No. 20, Sep. 26, 2000, pp. 10701-10705.
Burchill, et al., "Inhibition of interleukin-17 prevents the development of arthritis in vaccinated mice challenged with Borrelia burgdorferi", Infection and Immunity, vol. 71, No. 6, Jun. 2003, pp. 3437-3442.
Chabaud, M. et al., "Contribution of Interleukin 17 to Synovium Matrix Destruction in Rheumatoid Arthritis", Cytokine, Academic Press Ltd., vol. 12, No. 7, Jul. 2000, pp. 1092-1099.
Doo, et al., "CD4+ T cells regulate surgical and postinfection adhesion formation", The Journal Of Experimental Medicine, Jun. 3, 2002, vol. 195, No. 11, Jun. 3, 2002, pp. 1471-1478.
Davies, Julian, Affinity Improvement of Single Antibody VH Domains: Residues in All Three Hypervariable Regions Affect Antigen Binding, Sep. 1996, pp. 169-179, vol. 2, No. 3.
Dumont, F. J., "IL-17 cytokine/receptor families: Emerging targets for the modulation of inflammatory responses", Expert Opinion of Therapeutic Patents, Ashley Publications, GB vol. 13, No. 3, Mar. 1, 2003, pp. 287-3030.
Hellings, et al., "Interleukin-17 orchestrates the granulocyte influx into airways after allergen inhalation in a mouse model of allergic asthma", American Journal of Respiratory Cell and Molecular biology, vol. 28, No. 1, Jan. 2003, pp. 42-50.
Holt, Lucy J.: Domain Antibodies: Proteins for Therapy, Trends in Biotechnology, Nov. 2003, pp. 484-490, vol. 21, No. 11.
Kotake et al., "IL-17 in synovial fluids from patients with rheumatoid arthritis is a potent stimulator of osteoclastogenesis," The Journal of Clincial Investigation, 103(9):1345-1352 (May 1999).
Numasaki, et al., "Interleukin-17 promotes angiogenesis and tumor growth", Blood, vol. 101, No. 7, Apr. 1, 2003, pp. 2620-2627.
Pascalis, et al., "Grafting of 'abbreviated' complementary-determining regions containing specificity determining residues essential for ligand contact to engineer a less immunogenic hmanized monoclonal antibody", J. Immunol., 2002, 169:3076-3084.
Paul, "Fv Structure and Diversity in Three Dimensions", Fundamental Immunology, 3rd Edition, 1993, pp. 292-295.
R&D Systems: "Monoclonal Anti-Human IL-17 Antibody", Announcement R&D Systems, Jan. 11, 2004, pp. 1-2.
Thompson, et al., "Affinity maturation of a high-affinity human monoclonal antibody against the third hypervariable loop of human immunodeficiency virus: use of phage display to improve affiinity and broaden strain reactivity", Journal of Molecular Biology, vol. 256, No. 1, Feb. 16, 1996, pp. 77-88.

(Continued)

*Primary Examiner* — Dong Jiang
(74) *Attorney, Agent, or Firm* — McDonnell Boehnen Hulbert & Berghoff LLP

(57) ABSTRACT

The present invention relates neutralising epitopes of IL-17A and IL-17F and antibodies which bind those epitopes. The present invention also relates to the therapeutic uses of the antibody molecules and methods for producing them.

6 Claims, 5 Drawing Sheets

(56) References Cited

OTHER PUBLICATIONS

Figure 2A:
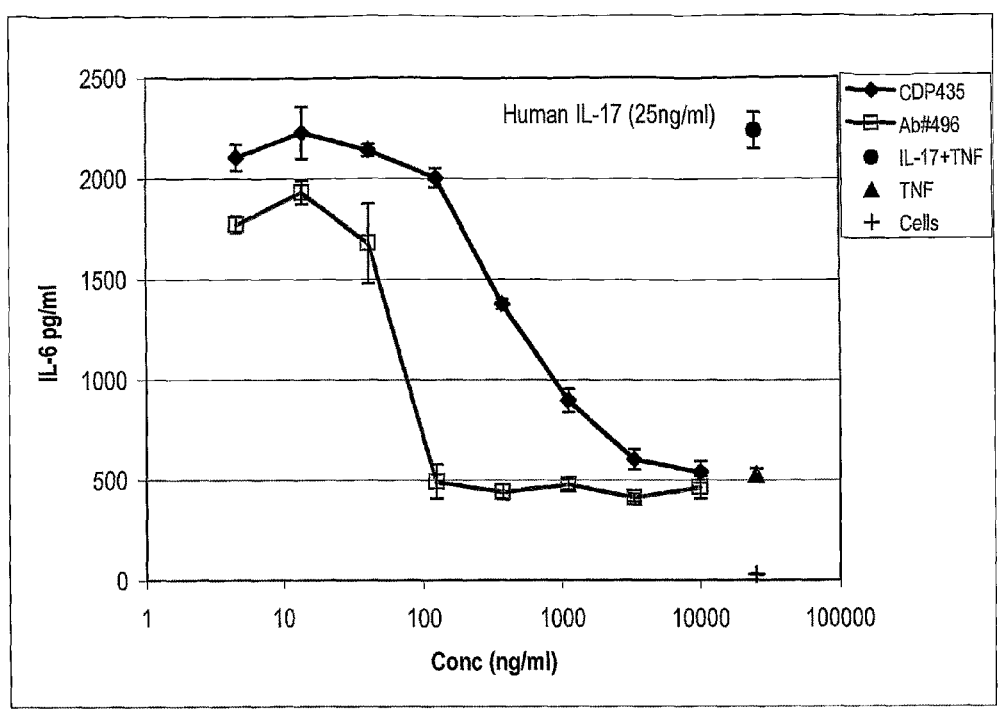

Vandamme et al.: Construction and characterization of a recombinant murine monoclonal antibody directed against human fibrin fragment-D dimer., J. Biochem. (1990) vol. 192, pp. 767-775.

PCT International Search Report of PCT International Application PCT/GB2007/003983 filed Oct. 18, 2007.
PCT International Search Report of PCT International Application PCT/GB2005/004392, dated Feb. 14, 2006.

* cited by examiner

Figure 1

(a) Light Chain variable region of antibody CA028_496 (SEQ ID NO:7)
AIQLTQSPSSLSASVGDRVTITCRADESVTTLMHWYQQKPGKAPKLLIYLVSNRESGVPSRF
SGSGSGTDFTLTISSLQPEDFATYYCQQTWSDPWTFGQGTKVEIKR (b) Heavy Chain variable region of antibody CA028_496 (SEQ ID NO:9)
EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
S (c)

| | |
|---|---|
| CDRH1: | GFTFSDYNMA (SEQ ID NO:1) |
| CDRH2: | TITYEGRNTYYRDSVKG (SEQ ID NO:2) |
| CDRH3: | PPQYYEGSIYRLWFAH (SEQ ID NO:3) |
| CDRL1: | RADESVTTLMH (SEQ ID NO:4) |
| CDRL2: | LVSNRES (SEQ ID NO:5) |
| CDRL3: | QQTWSDPWT (SEQ ID NO:6) |

(d) Light chain of antibody CA028_496 (SEQ ID NO:11)
AIQLTQSPSSLSASVGDRVTITCRADESVTTLMHWYQQKPGKAPKLLIYLVSNRESGVPSRF
SGSGSGTDFTLTISSLQPEDFATYYCQQTWSDPWTFGQGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (e) Heavy chain of antibody CA028_496 (SEQ ID NO:15)
EVQLVESGGGLVQPGGSLRLSCAASGFTFSDYNMAWVRQAPGKGLEWVATITYEGRNTYYRD
SVKGRFTISRDNAKNSLYLQMNSLRAEDTAVYYCASPPQYYEGSIYRLWFAHWGQGTLVTVS
SASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRVESKYGPPCPPCPAPEFLGGPSVFLF
PPKPKDTLMISRTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQEEMTKNQVSLTC
LVKGFYPSDIAVEWESNGQPENNYKTTPPVLDSDGSFFLYSRLTVDKSRWQEGNVFSCSVMH
EALHNHYTQKSLSLSLGK (f) DNA encoding light chain of antibody CA028_496 including signal sequence (SEQ ID NO:14)
atgtcagttcccacacaggtgctgggcctgcttctgttgtggctcaccgatgctaggtgtgc
catccagctgacccagagcccttcctctctcagcgccagtgtcggagacagagtgactatta
cctgcagggctgacgaaagcgtgaccacattgatgcactggtaccaacagaagcctggcaaa
gcccccaagctcctgatctatctggtttccaatcgggagtctggagtcccagcaggttcag
cggcagtgggtctggaactgactttaccctgacaatctcctcactccagcccgaagatttcg
ccacctactattgccagcagacttggagcgacccttggacatttggacagggcacaaaagtg
gagatcaagcgtacggtagcggccccatctgtcttcatcttcccgccatctgatgagcagtt
gaaatctggaactgcctctgttgtgtgcctgctgaataacttctatcccagagaggccaaag

Figure 1 continued tacagtggaaggtggataacgccctccaatcgggtaactcccaggagagtgtcacagagcag
gacagcaaggacagcacctacagcctcagcagcaccctgacgctgagcaaagcagactacga gaaacacaaagtctacgcctgcgaagtcacccatcagggcctgagctcgcccgtcacaaaga
gcttcaacaggggagagtgttag (g) DNA encoding heavy chain of antibody CA028_496 including signal sequence (SEQ ID NO:18)
atggaatggtcctgggtcttcctgttttcctttctgtcacaaccggggtgcacagcgaggt
tcagctcgttgaatccggaggcggactcgtgcagcctggggggctccttgcggctgagctgcg
ctgccagtggcttcactttcagcgattacaatatggcctgggtgcgccaggccccaggcaag
ggtctggagtgggtggccacaattacctatgagggcagaaacacttattaccgggattcagt
gaaagggcgatttaccatcagcagggataatgcaaagaacagtctgtacctgcagatgaact
ctctgagagctgaggacaccgctgtctactattgtgcaagcccaccccagtactatgagggc
tcaatctacagattgtggtttgcccattggggccagggaacactggtgaccgtctcgagcgc
ttctacaaagggcccatccgtcttccccctggcgccctgctccaggagcacctccgagagca
cagccgccctgggctgcctggtcaaggactacttccccgaaccggtgacggtgtcgtggaac
tcaggcgccctgaccagcggcgtgcacaccttcccggctgtcctacagtcctcaggactcta
ctccctcagcagcgtggtgaccgtgccctccagcagcttgggcacgaagacctacacctgca
acgtagatcacaagcccagcaacaccaaggtggacaagagagttggtgagaggccagcacag
ggagggagggtgtctgctggaagccaggctcagccctcctgcctggacgcaccccggctgtg
cagccccagccagggcagcaaggcatgccccatctgtctcctcacccggaggcctctgacc
accccactcatgcccagggagagggtcttctggatttttccaccaggctccgggcagccaca
ggctggatgcccctaccccaggccctgcgcatacaggggcaggtgctgcgctcagacctgcc
aagagccatatccgggaggaccctgcccctgacctaagcccaccccaaaggccaaactctcc
actccctcagctcagacaccttctctcctcccagatctgagtaactcccaatcttctctctg
cagagtccaaatatggtcccccatgccaccatgcccaggtaagccaacccaggcctcgccc
tccagctcaaggcgggacaggtgccctagagtagcctgcatccagggacaggccccagccgg
gtgctgacgcatccacctccatctcttcctcagcacctgagttcctggggggaccatcagtc
ttcctgttccccccaaaacccaaggacactctcatgatctcccggacccctgaggtcacgtg
cgtggtggtggacgtgagccaggaagaccccgaggtccagttcaactggtacgtggatggcg
tggaggtgcataatgccaagacaaagccgcgggaggagcagttcaacagcacgtaccgtgtg
gtcagcgtcctcaccgtcctgcaccaggactggctgaacggcaaggagtacaagtgcaaggt
ctccaacaaaggcctcccgtcctccatcgagaaaaccatctccaaagccaaaggtgggaccc
acggggtgcgagggccacatggacagaggtcagctcggcccaccctctgccctgggagtgac
cgctgtgccaacctctgtccctacagggcagccccgagagccacaggtgtacaccctgcccc
catcccaggaggagatgaccaagaaccaggtcagcctgacctgcctggtcaaaggcttctac
cccagcgacatcgccgtggagtgggagagcaatgggcagccggagaacaactacaagaccac
gcctcccgtgctggactccgacggctccttcttcctctacagcaggctaaccgtggacaaga
gcaggtggcaggaggggaatgtcttctcatgctccgtgatgcatgaggctctgcacaaccac
tacacacagaagagcctctccctgtctctgggtaaa

Figure 1 continued (h) Human IL-17A (SEQ ID NO:21)

GITIPRNPGCPNSEDKNFPRTVMVNLNIHNRNTNTNPKRSSDYYNRSTSPWNLHRNEDPERY
PSVIWEAKCRHLGCINADGNVDYHMNSVPIQQEILVLRREPPHCPNSFRLEKILVSVGCTCV
TPIVHHVA (i) Human IL-17F (SEQ ID NO:22)

RKIPKVGHTFFQKPESCPPVPGGSMKLDIGIINENQRVSMSRNIESRSTSPWNYTVTWDPNR
YPSEVVQAQCRNLGCINAQGKEDISMNSVPIQQETLVVRRKHQGCSVSFQLEKVLVTVGCTC
VTPVIHHVQ

```
                        SEQUENCE LISTING

<160> NUMBER OF SEQ ID NOS: 24

<210> SEQ ID NO 1
<211> LENGTH: 10
<212> TYPE: PRT
<213> ORGANISM: Artificial sequence
<220> FEATURE:
<223> OTHER INFORMATION: derived from Rattus

<400> SEQUENCE: 1

Gly Phe Thr Phe Ser Asp Tyr Asn Met Ala
1               5                   10

<210> SEQ ID NO 2
<211> LENGTH: 17
<212> TYPE: PRT
<213> ORGANISM: Artificial sequence
<220> FEATURE:
<223> OTHER INFORMATION: derived from Rattus

<400> SEQUENCE: 2

Thr Ile Thr Tyr Glu Gly Arg Asn Thr Tyr Tyr Arg Asp Ser Val Lys
1               5                   10                  15

Gly
```

```
<210> SEQ ID NO 3
<211> LENGTH: 16
<212> TYPE: PRT
<213> ORGANISM: Artificial sequence
<220> FEATURE:
<223> OTHER INFORMATION: derived from Rattus

<400> SEQUENCE: 3

Pro Pro Gln Tyr Tyr Glu Gly Ser Ile Tyr Arg Leu Trp Phe Ala His
1               5                   10                  15

<210> SEQ ID NO 4
<211> LENGTH: 11
<212> TYPE: PRT
<213> ORGANISM: Artificial sequence
<220> FEATURE:
<223> OTHER INFORMATION: derived from Rattus

<400> SEQUENCE: 4

Arg Ala Asp Glu Ser Val Thr Thr Leu Met His
1               5                   10

<210> SEQ ID NO 5
<211> LENGTH: 7
<212> TYPE: PRT
<213> ORGANISM: Artificial sequence
<220> FEATURE:
<223> OTHER INFORMATION: derived from Rattus

<400> SEQUENCE: 5

Leu Val Ser Asn Arg Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: derived from Rattus

<400> SEQUENCE: 6

Gln Gln Thr Trp Ser Asp Pro Trp Thr
1               5

<210> SEQ ID NO 7
<211> LENGTH: 108
<212> TYPE: PRT
<213> ORGANISM: Artificial sequence
<220> FEATURE:
<223> OTHER INFORMATION: CDRs derived from Rattus

<400> SEQUENCE: 7

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95
```

-continued

```
Thr Phe Gly Gln Gly Thr Lys Val Glu Ile Lys Arg
            100                 105

<210> SEQ ID NO 8
<211> LENGTH: 4
<212> TYPE: PRT
<213> ORGANISM: Artificial sequence
<220> FEATURE:
<223> OTHER INFORMATION: derived from IL-17

<400> SEQUENCE: 8

Ser Met Ser Arg
1

<210> SEQ ID NO 9
<211> LENGTH: 125
<212> TYPE: PRT
<213> ORGANISM: Artificial sequence
<220> FEATURE:
<223> OTHER INFORMATION: CDRs derived from Rattus

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser
        115                 120                 125

<210> SEQ ID NO 10
<211> LENGTH: 4
<212> TYPE: PRT
<213> ORGANISM: Artificial seqence
<220> FEATURE:
<223> OTHER INFORMATION: derived from IL-17

<400> SEQUENCE: 10

Cys Arg Asn Leu
1

<210> SEQ ID NO 11
<211> LENGTH: 214
<212> TYPE: PRT
<213> ORGANISM: Artificial sequence
<220> FEATURE:
<223> OTHER INFORMATION: derive from at least from Rattus

<400> SEQUENCE: 11

Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30
```

```
Met His Trp Tyr Gln Gln Lys Pro Gly Lys Ala Pro Lys Leu Leu Ile
            35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Trp Ser Asp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 12
<211> LENGTH: 10
<212> TYPE: PRT
<213> ORGANISM: Artificial sequence
<220> FEATURE:
<223> OTHER INFORMATION: derived from IL-17

<400> SEQUENCE: 12

Lys Glu Asp Ile Ser Met Asn Ser Val Pro
1               5                   10

<210> SEQ ID NO 13
<211> LENGTH: 4
<212> TYPE: PRT
<213> ORGANISM: Artificial sequence
<220> FEATURE:
<223> OTHER INFORMATION: derived from IL-17

<400> SEQUENCE: 13

Val Thr Pro Val
1

<210> SEQ ID NO 14
<211> LENGTH: 705
<212> TYPE: DNA
<213> ORGANISM: Artificial sequence
<220> FEATURE:
<223> OTHER INFORMATION: CDRs encoded derived from Rattus

<400> SEQUENCE: 14
atgtcagttc ccacacaggt gctgggcctg cttctgttgt ggcttaccga tgctaggtgt      60
gccatccagc tgacccagag cccttcctct ctcagcgcca gtgtcggaga cagagtgact     120
attacctgca gggctgacga aagcgtgacc acattgatgc actggtacca acagaagcct     180
ggcaaagccc ccaagctcct gatctatctg gtttccaatc gggagtctgg agtccccagc     240
```

```
aggttcagcg gcagtgggtc tggaactgac tttaccctga caatctcctc actccagccc    300
gaagatttcg ccacctacta ttgccagcag acttggagcg acccttggac atttggacag    360
ggcacaaaag tggagatcaa gcgtacggta gcggccccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttag                    705
```

<210> SEQ ID NO 15
<211> LENGTH: 452
<212> TYPE: PRT
<213> ORGANISM: Artificial sequence
<220> FEATURE:
<223> OTHER INFORMATION: derived from at least Rattus

<400> SEQUENCE: 15

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Asn Met Ala Trp Val Arg Gln Ala Pro Gly Lys Gly Leu Glu Trp Val
        35                  40                  45

Ala Thr Ile Thr Tyr Glu Gly Arg Asn Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gln Tyr Tyr Glu Gly Ser Ile Tyr Arg Leu Trp Phe
            100                 105                 110

Ala His Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285
```

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Gln Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
        420                 425                 430

Met His Glu Ala Leu His Asn His Tyr Thr Gln Lys Ser Leu Ser Leu
    435                 440                 445

Ser Leu Gly Lys
    450

<210> SEQ ID NO 16

<400> SEQUENCE: 16

000

<210> SEQ ID NO 17

<400> SEQUENCE: 17

000

<210> SEQ ID NO 18
<211> LENGTH: 2020
<212> TYPE: DNA
<213> ORGANISM: Artificial sequence
<220> FEATURE:
<223> OTHER INFORMATION: CDRs encoded derived from Rattus

<400> SEQUENCE: 18
atggaatggt cctgggtctt cctgtttttc ctttctgtca caaccggggt gcacagcgag      60
gttcagctcg ttgaatccgg aggcggactc gtgcagcctg ggggctcctt gcggctgagc     120
tgcgctgcca gtggcttcac tttcagcgat tacaatatgg cctgggtgcg ccaggcccca     180
ggcaagggtc tggagtgggt ggccacaatt acctatgagg cagaaacact tattaccgg      240 gattcagtga aaggcgatt taccatcagc agggataatg caaagaacag tctgtacctg     300
cagatgaact ctctgagagc tgaggacacc gctgtctact attgtgcaag cccaccccag     360
tactatgagg gctcaatcta cagattgtgg tttgcccatt ggggccaggg aacactggtg     420
accgtctcga gcgcttctac aaagggccca tccgtcttcc ccctggcgcc ctgctccagg     480
agcacctccg agagcacagc cgccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc agcagcttg      660 ggcacgaaga cctacacctg caacgtagat cacaagccca gcaacaccaa ggtggacaag     720

```
agagttggtg agaggccagc acagggaggg agggtgtctg ctggaagcca ggctcagccc      780
tcctgcctgg acgcacccg gctgtgcagc cccagcccag ggcagcaagg catgccccat       840
ctgtctcctc acccggaggc ctctgaccac cccactcatg cccagggaga gggtcttctg      900 gattttcca ccaggctccg ggcagccaca ggctggatgc ccctaccca ggccctgcgc        960 atacaggggc aggtgctgcg ctcagacctg ccaagagcca tatccgggag acccctgccc     1020
ctgacctaag cccacccaa aggccaaact ctccactccc tcagctcaga caccttctct      1080
cctcccagat ctgagtaact cccaatcttc tctctgcaga gtccaaatat ggtccccat     1140 gcccaccatg cccaggtaag ccaacccagg cctcgccctc cagctcaagg cgggacaggt    1200
gccctagagt agcctgcatc cagggacagg ccccagccgg gtgctgacgc atccacctcc    1260
atctcttcct cagcacctga gttcctgggg ggaccatcag tcttcctgtt ccccccaaaa    1320
cccaaggaca ctctcatgat ctcccggacc cctgaggtca cgtgcgtggt ggtggacgtg    1380
agccaggaag accccgaggt ccagttcaac tggtacgtgg atggcgtgga ggtgcataat    1440
gccaagacaa agccgcggga ggagcagttc aacagcacgt accgtgtggt cagcgtcctc    1500
accgtcctgc accaggactg gctgaacggc aaggagtaca agtgcaaggt ctccaacaaa    1560
ggcctcccgt cctccatcga gaaaaccatc tccaaagcca aggtgggac ccacggggtg     1620 cgagggccac atggacagag gtcagctcgg cccacccttct gccctgggag tgaccgctgt    1680
gccaacctct gtccctacag ggcagccccg agagccacag gtgtacaccc tgcccccatc    1740
ccaggaggag atgaccaaga accaggtcag cctgacctgc ctggtcaaag gcttctaccc    1800
cagcgacatc gccgtggagt gggagagcaa tgggcagccg gagaacaact acaagaccac    1860 gcctccgtg ctggactccg acggctcctt cttcctctac agcaggctaa ccgtggacaa     1920
gagcaggtgg caggagggga atgtcttctc atgctccgtg atgcatgagg ctctgcacaa    1980
ccactacaca cagaagagcc tctccctgtc tctgggtaaa                          2020
```

<210> SEQ ID NO 19
<211> LENGTH: 286
<212> TYPE: PRT
<213> ORGANISM: Artificial sequence
<220> FEATURE:
<223> OTHER INFORMATION: Recombinant IL-17A/F heterodimer was produced
      by linking IL-17A and IL-17F using a GS linker.

<400> SEQUENCE: 19

```
Met Gly Ile Thr Ile Pro Arg Asn Pro Gly Cys Pro Asn Ser Glu Asp
1               5                   10                  15

Lys Asn Phe Pro Arg Thr Val Met Val Asn Leu Asn Ile His Asn Arg
            20                  25                  30

Asn Thr Asn Thr Asn Pro Lys Arg Ser Ser Asp Tyr Tyr Asn Arg Ser
        35                  40                  45

Thr Ser Pro Trp Asn Leu His Arg Asn Glu Asp Pro Glu Arg Tyr Pro
    50                  55                  60

Ser Val Ile Trp Glu Ala Lys Cys Arg His Leu Gly Cys Ile Asn Ala
65                  70                  75                  80

Asp Gly Asn Val Asp Tyr His Met Asn Ser Val Pro Ile Gln Gln Glu
                85                  90                  95

Ile Leu Val Leu Arg Arg Glu Pro Pro His Cys Pro Asn Ser Phe Arg
            100                 105                 110

Leu Glu Lys Ile Leu Val Ser Val Gly Cys Thr Cys Val Thr Pro Ile
        115                 120                 125
```

```
Val His His Val Ala Gly Gly Gly Ser Gly Gly Gly Ser Gly
    130                 135                 140

Gly Gly Gly Ser Gly Gly Gly Ser Arg Lys Ile Pro Lys Val Gly
145                 150                 155                 160

His Thr Phe Phe Gln Lys Pro Glu Ser Cys Pro Pro Val Pro Gly Gly
                165                 170                 175

Ser Met Lys Leu Asp Ile Gly Ile Ile Asn Glu Asn Gln Arg Val Ser
                180                 185                 190

Met Ser Arg Asn Ile Glu Ser Arg Ser Thr Ser Pro Trp Asn Tyr Thr
            195                 200                 205

Val Thr Trp Asp Pro Asn Arg Tyr Pro Ser Glu Val Val Gln Ala Gln
            210                 215                 220

Cys Arg Asn Leu Gly Cys Ile Asn Ala Gln Gly Lys Glu Asp Ile Ser
225                 230                 235                 240

Met Asn Ser Val Pro Ile Gln Gln Glu Thr Leu Val Val Arg Arg Lys
                245                 250                 255

His Gln Gly Cys Ser Val Ser Phe Gln Leu Glu Lys Val Leu Val Thr
                260                 265                 270

Val Gly Cys Thr Cys Val Thr Pro Val Ile His His Val Gln
                275                 280                 285
```

<210> SEQ ID NO 20
<211> LENGTH: 134
<212> TYPE: PRT
<213> ORGANISM: Artificial sequence
<220> FEATURE:
<223> OTHER INFORMATION: Recombinant cynomolgus IL-17F

<400> SEQUENCE: 20

```
Met Arg Lys Ile Pro Lys Val Gly His Thr Phe Phe Gln Lys Pro Glu
1               5                   10                  15

Ser Cys Pro Pro Val Pro Glu Gly Ser Met Lys Leu Asp Thr Gly Ile
                20                  25                  30

Ile Asn Glu Asn Gln Arg Val Ser Met Ser Arg Asn Ile Glu Ser Arg
            35                  40                  45

Ser Thr Ser Pro Trp Asn Tyr Thr Val Thr Trp Asp Pro Asn Arg Tyr
50                  55                  60

Pro Ser Glu Val Val Gln Ala Gln Cys Lys His Leu Gly Cys Ile Asn
65                  70                  75                  80

Ala Gln Gly Lys Glu Asp Ile Ser Met Asn Ser Val Pro Ile Gln Gln
                85                  90                  95

Glu Thr Leu Val Leu Arg Arg Lys His Gln Gly Cys Ser Val Ser Phe
            100                 105                 110

Gln Leu Glu Lys Val Leu Val Thr Val Gly Cys Thr Cys Val Thr Pro
            115                 120                 125

Val Ile His His Val Gln
            130
```

<210> SEQ ID NO 21
<211> LENGTH: 132
<212> TYPE: PRT
<213> ORGANISM: Homo sapiens

<400> SEQUENCE: 21

```
Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
                20                  25                  30
```

```
Thr Asn Thr Asn Pro Lys Arg Ser Asp Tyr Tyr Asn Arg Ser Thr
            35                  40                  45

Ser Pro Trp Asn Leu His Arg Asn Glu Asp Pro Glu Arg Tyr Pro Ser
 50                  55                  60

Val Ile Trp Glu Ala Lys Cys Arg His Leu Gly Cys Ile Asn Ala Asp
 65                  70                  75                  80

Gly Asn Val Asp Tyr His Met Asn Ser Val Pro Ile Gln Gln Glu Ile
                    85                  90                  95

Leu Val Leu Arg Arg Glu Pro Pro His Cys Pro Asn Ser Phe Arg Leu
                100                 105                 110

Glu Lys Ile Leu Val Ser Val Gly Cys Thr Cys Val Thr Pro Ile Val
            115                 120                 125

His His Val Ala
        130

<210> SEQ ID NO 22
<211> LENGTH: 133
<212> TYPE: PRT
<213> ORGANISM: Homo sapiens

<400> SEQUENCE: 22

Arg Lys Ile Pro Lys Val Gly His Thr Phe Phe Gln Lys Pro Glu Ser
 1               5                  10                  15

Cys Pro Pro Val Pro Gly Gly Ser Met Lys Leu Asp Ile Gly Ile Ile
                20                  25                  30

Asn Glu Asn Gln Arg Val Ser Met Ser Arg Asn Ile Glu Ser Arg Ser
            35                  40                  45

Thr Ser Pro Trp Asn Tyr Thr Val Thr Trp Asp Pro Asn Arg Tyr Pro
 50                  55                  60

Ser Glu Val Val Gln Ala Gln Cys Arg Asn Leu Gly Cys Ile Asn Ala
 65                  70                  75                  80

Gln Gly Lys Glu Asp Ile Ser Met Asn Ser Val Pro Ile Gln Gln Glu
                    85                  90                  95

Thr Leu Val Val Arg Arg Lys His Gln Gly Cys Ser Val Ser Phe Gln
                100                 105                 110

Leu Glu Lys Val Leu Val Thr Val Gly Cys Thr Cys Val Thr Pro Val
            115                 120                 125

Ile His His Val Gln
        130

<210> SEQ ID NO 23
<211> LENGTH: 445
<212> TYPE: PRT
<213> ORGANISM: Artificial sequence
<220> FEATURE:
<223> OTHER INFORMATION: derived from at least Rattus and Murine origin

<400> SEQUENCE: 23

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
                20                  25                  30

Asn Met Ala Trp Val Arg Gln Ala Pro Gly Lys Gly Leu Glu Trp Val
            35                  40                  45

Ala Thr Ile Thr Tyr Glu Gly Arg Asn Thr Tyr Tyr Arg Asp Ser Val
 50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Ala Ser Pro Pro Gln Tyr Tyr Glu Gly Ser Ile Tyr Arg Leu Trp Phe
                100                 105                 110

Ala His Trp Gly Gln Gly Thr Leu Val Thr Val Ser Ser Ala Lys Thr
            115                 120                 125

Thr Pro Pro Ser Val Tyr Pro Leu Ala Pro Gly Ser Ala Ala Gln Thr
        130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
                180                 185                 190

Val Thr Val Pro Ser Ser Thr Trp Pro Ser Glu Thr Val Thr Cys Asn
            195                 200                 205

Val Ala His Pro Ala Ser Ser Thr Lys Val Asp Lys Lys Ile Val Pro
        210                 215                 220

Arg Asp Cys Gly Cys Ala Ala Ala Ile Gln Leu Thr Gln Ser Pro Ser
225                 230                 235                 240

Ser Leu Ser Ala Ser Val Gly Asp Arg Val Thr Ile Thr Cys Arg Ala
                245                 250                 255

Asp Glu Ser Val Thr Thr Leu Met His Trp Tyr Gln Gln Lys Pro Gly
                260                 265                 270

Lys Ala Pro Lys Leu Leu Ile Tyr Leu Val Ser Asn Arg Glu Ser Gly
            275                 280                 285

Val Pro Ser Arg Phe Ser Gly Ser Gly Ser Gly Thr Asp Phe Thr Leu
        290                 295                 300

Thr Ile Ser Ser Leu Gln Pro Glu Asp Phe Ala Thr Tyr Tyr Cys Gln
305                 310                 315                 320

Gln Thr Trp Ser Asp Pro Trp Thr Phe Gly Gln Gly Thr Lys Val Glu
                325                 330                 335

Ile Lys Arg Thr Asp Ala Ala Pro Thr Val Ser Ile Phe Pro Pro Ser
                340                 345                 350

Ser Glu Gln Leu Thr Ser Gly Gly Ala Ser Val Val Cys Phe Leu Asn
            355                 360                 365

Asn Phe Tyr Pro Lys Asp Ile Asn Val Lys Trp Lys Ile Asp Gly Ser
        370                 375                 380

Glu Arg Gln Asn Gly Val Leu Asn Ser Trp Thr Asp Gln Asp Ser Lys
385                 390                 395                 400

Asp Ser Thr Tyr Ser Met Ser Ser Thr Leu Thr Leu Thr Lys Asp Glu
                405                 410                 415

Tyr Glu Arg His Asn Ser Tyr Thr Cys Glu Ala Thr His Lys Thr Ser
                420                 425                 430

Thr Ser Pro Ile Val Lys Ser Phe Asn Arg Asn Glu Cys
            435                 440                 445

<210> SEQ ID NO 24
<211> LENGTH: 107
<212> TYPE: PRT
<213> ORGANISM: Artificial sequence
<220> FEATURE:
<223> OTHER INFORMATION: derived from at least Rattus and Murine

<400> SEQUENCE: 24
```

```
Ala Ile Gln Leu Thr Gln Ser Pro Ser Ser Leu Ser Ala Ser Val Gly
1               5                   10                  15

Asp Arg Val Thr Ile Thr Cys Arg Ala Asp Glu Ser Val Thr Thr Leu
            20                  25                  30

Met His Trp Tyr Gln Gln Lys Pro Gly Lys Ala Pro Lys Leu Leu Ile
        35                  40                  45

Tyr Leu Val Ser Asn Arg Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                      75                  80

Glu Asp Phe Ala Thr Tyr Tyr Cys Gln Gln Thr Trp Ser Asp Pro Trp
                85              90                      95

Thr Phe Gly Gln Gly Thr Lys Val Glu Ile Lys
            100                 105
```

ANTIBODIES SPECIFIC TO IL-17A AND IL-17F

This is a National Stage of International Application No. PCT/GB09/001,026, filed Apr. 22, 2009, which claims priority to GB application No. 0807413.0, filed on Apr. 23, 2008.

The present invention relates to neutralising epitopes of IL-17A and IL-17F and antibodies which bind those epitopes. The present invention also relates to the therapeutic uses of the antibody molecules and methods for producing them.

Interleukin 17 (IL-17), also known as CTLA-8 or IL-17A, is a pro-inflammatory cytokine which stimulates the secretion of a wide range of other cytokines from various non-immune cells. IL-17A is capable of inducing the secretion of IL-6, IL-8, PGE2, MCP-1 and G-CSF by adherent cells like fibroblasts, keratinocytes, epithelial and endothelial cells and is also able to induce ICAM-1 surface expression, proliferation of T cells, and growth and differentiation of CD34+ human progenitors into neutrophils when cocultured in the presence of irradiated fibroblasts (Fossiez et al., 1998, Int. Rev. Immunol. 16, 541-551). IL-17A is predominantly produced by activated memory T cells and acts by binding to a ubiquitously distributed cell surface receptor (IL-17R) (Yao et al., 1997, Cytokine, 9, 794-800). It may also act through binding to a complex of IL-17RA and IL-17RC (Toy et al., 2006, J. Immunol. 177(11);36-39). IL-17 producing T cells called 'TH17 cells' have been implicated in the pathogenesis of certain cancers (Weaver et al., 2006, Immunity, 24, 677-688; Langowski et al., 2006, 442, 461-465; Iwakura and Ishigame, 2006, J. Clin. Invest. 116, 5, 1218-1222).

A number of homologues of IL-17 have been identified which have both similar and distinct roles in regulating inflammatory responses. For a review of IL-17 cytokine/receptor families see Dumont, 2003, Expert Opin. Ther. Patents, 13, 287-303. One such homologue is IL-17F, also known as IL-24 and ML-1, which is around 55% identical to IL-17A and is thought to share the same receptors as IL-17A (Dolls and Linden 2004, Immunity, 21, 467-476; Hymowitz, et al., 2001, EMBO J. 20(19), 5332-5341; Kuestner et al., 2007, Journal of Immunology, 179, 5462-5473).

Both IL-17A and IL-17F can form both homodimeric and heterodimeric proteins, all of which are produced by activated human CD4+ T cells (Wright et al., 2007, J Biol Chem. 282 (18), 13447-13455).

IL-17 may contribute to a number of diseases mediated by abnormal immune responses, such as rheumatoid arthritis and air-way inflammation, as well as organ transplant rejection and antitumour immunity. Inhibitors of IL-17 activity are well known in the art for example a murine IL-17R: human Fc fusion protein, a murine soluble IL-17R and an anti-IL-17 monoclonal antibody have been used to demonstrate the role of IL-17 in various models of rheumatoid arthritis (Lubberts et al., J. Immunol. 2001, 167, 1004-1013; Chabaud et al., Arthritis Res. 2001, 3, 168-177). In addition, neutralising polyclonal antibodies have been used to reduce peritoneal adhesion formation (Chung et al., 2002, J. Exp. Med., 195, 1471-1478). Rat derived anti-human IL-17A antibodies were described in WO04/106377. A humanised anti-IL-17A antibody with an affinity of around 220 pM was described in WO2006/054059. A monoclonal anti-IL-17A fully human antibody with an affinity of around 188 pM was described in WO2006/013107.

International patent application WO2008/001063 describes a high affinity neutralising anti-IL-17A antibody, CA048_497. Other neutralising antibodies which bind IL-17A have been described in WO2007/070750 and WO2007/149032.

Antibodies which bind IL-17F and IL-17A/IL-17F heterodimers were described in WO2006/088833. Antibodies which specifically bind the IL-17A/IL-17F heterodimer were described in WO2005/010044.

IL-17F antagonism has been associated with protection against asthma (Kawaguchi et al., 2006, J. Allergy Clin. Immunol. 117(4); 795-801) and IL-17F is also thought to play a role in arthritis pathology (Lubberts 2003, Current Opinion in Investigational Drugs, 4 (5), 572-577).

Accordingly dual antagonists of IL-17A and IL-17F may be more effective than a sole antagonist in treating IL-17 mediated diseases. Antibodies which bind IL-17A and IL-17F were described in WO2007/106769. International patent application PCT/GB2007/003983 (international filing date 18 Oct. 2007) describes a high affinity antibody, CA048_496 which binds human IL-17A, IL-17F and IL-17A/F heterodimer, the sequence of which is provided herein below.

The present invention provides novel neutralising epitopes on IL-17A and IL-17F and antibodies which bind to, and/or interact with, those epitopes.

In one embodiment the present invention provides a neutralising epitope of IL-17A which comprises or consists of one or more of the residues, eg. two or more, e.g. three or more, e.g. four or more, selected from the group consisting of TYR44, ASN45, TRP51, ASN52 and ASP84 of human IL-17A (SEQ ID NO:21).

In one embodiment the present invention provides a neutralising epitope of IL-17A which comprises or consists of one or more of the residues selected from the group consisting of SER41, TYR44, ASN45, TRP51, ASN52, HIS54, ARG72, HIS73 and ASP84 of human IL-17A (SEQ ID NO:21).

In one embodiment, the present invention provides a neutralising epitope of IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:21).

In one embodiment, the present invention provides a neutralising epitope of IL-17A which comprises one or more of the residues, eg. two or more, e.g. three or more, e.g. four or more selected from the group consisting of TYR44, ASN45, TRP51, ASN52 and ASP84 of human IL-17A (SEQ ID NO:21) and optionally one or more of the residues selected from the group consisting of SER41, ARG46, HIS54, ARG72, HIS73, HIS86, VAL128, HIS129 and VAL131 of human IL-17A (SEQ ID NO:21).

In one embodiment, the present invention provides a neutralising epitope of IL-17A which comprises amino acid residues TYR44, ASN45, TRP51, ASN52 and ASP84 of human IL-17A (SEQ ID NO:21) and optionally one or more of the residues selected from the group consisting of SER41, ARG46, HIS54, ARG72, HIS73, HIS86, VAL128, HIS129 and VAL131 of human IL-17A (SEQ ID NO:21).

In one embodiment, the neutralising epitope provided by the present invention does not comprise one or more of the amino acid residues selected from the group consisting of ASP80, GLY81 and ASN82 of human IL-17A (SEQ ID NO:21).

In one embodiment, the neutralising epitope provided by the present invention does not comprise one or more of the amino acid residues selected from the group consisting of ASP80, GLY81, ASN82 and VAL83 of human IL-17A (SEQ ID NO:21).

The present invention also provides a novel neutralising epitope of human IL-17F (SEQ ID NO:22) which comprises or consists of one or more e.g. three or more, e.g. five or more, e.g. ten or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

The present invention also provides a novel neutralising epitope of human IL-17F (SEQ ID NO:22) which comprises or consists of one or more e.g. three or more, e.g. five or more, e.g. ten or more of the following residues: SER39, MET40, SER41, ARG42, ARG47, ASN53, CYS72, ARG73, ASN74, LEU75, LYS83, GLU84, ASP85, ILE86, SER87, MET88, ASN89, SER90, VAL91, PRO92, GLN94, THR119, CYS122, VAL125, THR126, PRO127, VAL128.

In one embodiment the neutralising epitope of human IL-17F (SEQ ID NO:22) comprises or consists of one or more e.g. three or more, e.g. five or more, e.g. ten or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

In one embodiment the neutralising epitope of human IL-17F (SEQ ID NO:22) comprises or consists of (or further comprises or further consists of) one or more e.g. three or four of the following residues: GLN71, CYS72, ILE86, ASN89, SER90 and VAL128 for example from a first chain in an IL17f dimer.

In one embodiment the neutralising epitope of human IL-17F (SEQ ID NO:22) comprises or consists of (or further comprises or further consists of) one a residue: ARG47 for example from a second chain in an IL17f dimer.

In one embodiment the neutralising epitope of human IL-17F (SEQ ID NO:22) comprises or consists of one or more e.g. three or more, e.g. five or more, e.g. ten or more of the following residues: GLN71, CYS72, ASN74, LEU75, ILE86, ASN89, SER90, PRO92, VAL128, HIS131 and GLN133 for example from a first chain in an IL17f dimer.

In one embodiment the neutralising epitope of human IL-17F (SEQ ID NO:22) comprises or consists of (or further comprises or further consists of) one or more e.g. three or four of the following residues: ARG37, SER39, SER41 and ARG47 for example from a second chain in an IL17f dimer.

In one embodiment the neutralising epitope of human IL-17F (SEQ ID NO:22) comprises or consists of one or more e.g. three or more, e.g. five or more, e.g. ten or more of the following residues: GLN71, CYS72, ARG73, ASN74, LEU75, ILE86, SER87 ASN89, SER90, VAL91, PRO92, VAL128, HIS131 and GLN133, for example from a first chain in an IL17f dimer.

In one embodiment the neutralising epitope of human IL-17F (SEQ ID NO:22) comprises or consists of (or further comprises or further consists of) one or more e.g. three or four of the following residues: ASN33, GLN36, ARG37, SER39, SER41, ARG42, ILE44 and ARG47 for example from a second chain in an IL17f dimer.

In one embodiment the neutralising epitope of human IL-17F (SEQ ID NO:22) comprises or consists of one or more e.g. three or more, e.g. five or more, e.g. ten or more of the following residues: GLN12, LYS13, SER24, ISO32, ASN33 GLU34, ASN35, GLN36, VAL38, SER46, ASN53, TYR54, GLN69, ISO78, ASP85, SER87, MET88, ASM89, GLN94, LYS103 and THR126.

In one embodiment the neutralising epitope of human IL-17F (SEQ ID NO:22) comprises or consists of one or more e.g. three or more, e.g. five or more, e.g. ten or more of the following residues: GLN12, SER24, ASN33, GLU34, GLN36, VAL38, ASN53, TYR54, ASP85, MET88, ASM89, and THR126.

In one embodiment the neutralising epitope of human IL-17F (SEQ ID NO:22) comprises or consists of one or more e.g. three or four of the following residues: GLN12, SER24, ASN33, GLU34, ASP85 and MET88.

In one embodiment the neutralising epitope of human IL-17F (SEQ ID NO:22) comprises or consists of amino acids V33 to V38 inclusive.

In one embodiment the neutralising epitope of human IL-17F (SEQ ID NO:22) comprises or consists of amino acids V87 to Q94 inclusive.

In one embodiment the neutralising epitope of IL-17F further comprises one or more of the following residues: ILE129, HIS130, H131, V132, Q133.

In one embodiment there is provided one or more neutralising epitope of human IL-17F (SEQ ID NO:22) each independently comprises or consists of amino acids V33 to V38 inclusive and/or V87 to Q94 inclusive.

In one embodiment the epitope is defined as amino acid residues located within 4 Å, 3.5 Å or 3.0 Å of a binding entity, such as an antibody or fragment.

The present invention also provides epitopic fragments of IL-17A that can be used, if required, as an immunogen to obtain neutralising antibodies which bind to the neutralising epitope of IL-17A. For example epitopic fragments comprising one or more of the amino acid residues of IL-17A provided herein above, may be used as an immunogen.

The present invention also provides epitopic fragments of IL-17F that can be used, if required, as an immunogen to obtain neutralising antibodies which bind to the neutralising epitope of IL-17F. For example epitopic fragments comprising one or more of the amino acid residues of IL-17F provided herein above, may be used as an immunogen.

The present invention also provides antibodies which bind to, and/or interact with, a neutralising epitope provided by the present invention. It will be appreciated that an antibody can interact directly or indirectly with an epitope of the present invention, e.g. by direct binding or by allosteric interaction.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment the antibodies of the present invention specifically bind to IL-17A. Specifically binding means that the antibodies have a greater affinity for IL-17A polypeptides than for other polypeptides. In one embodiment the antibodies of the present invention specifically bind to IL-17F. Specifically binding means that the antibodies have a greater affinity for IL-17F polypeptides than for other polypeptides. In a preferred embodiment the antibodies of the present invention specifically bind to IL-17A and IL-17F. Specifically binding means that the antibodies have a greater affinity for IL-17A and IL-17F polypeptides (including the IL-17A/IL-17F heterodimer) than for other polypeptides. Preferably the IL-17A and IL-17F polypeptides are human. In one embodiment the antibody also binds cynomolgus IL-17A and/or IL-17F.

Where an antibody of the present invention binds human IL-17A and human IL-17F the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

As used herein, the term 'neutralising antibody' describes an antibody that is capable of neutralising the biological signalling activity of IL-17A and/or IL17F and/or IL-17A/F heterodimer, for example by blocking binding of IL-17A and/or IL17F to one or more of their receptors and by blocking binding of the IL-17A/IL-17F heterodimer to one or more of its receptors. It will be appreciated that the term 'neutralising' as used herein refers to a reduction in biological signalling activity which may be partial or complete. Further, it will be appreciated that the extent of neutralisation of IL-17A and IL-17F activity by an antibody which binds both IL-17A and IL-17F may be the same or different. In one embodiment the extent of neutralisation of the activity of the IL-17A/IL-17F heterodimer may be the same or different as the extent of neutralisation of IL-17A or IL-17F activity.

In one embodiment the invention provides antibodies which bind to, and/or interact with, a neutralising epitope of IL-17A provided by the present invention.

Accordingly, in one embodiment the present invention provides a neutralising antibody which binds human IL-17A that binds to, and/or interacts with, an epitope of human IL-17A comprising or consisting of one or more e.g. two or more or three or more of the residues selected from the group consisting of TYR44, ASN45, TRP51, ASN52 and ASP84 of human IL-17A (SEQ ID NO:21).

In one embodiment the present invention provides a neutralising antibody which binds human IL-17A that binds to an epitope of human IL-17A comprising ASN52 of human IL-17A (SEQ ID NO:21).

In one embodiment the present invention provides a neutralising antibody which binds human IL-17A that binds to an epitope of human IL-17A comprising ASN52 and ASP84 of human IL-17A (SEQ ID NO:21).

In one embodiment, the present invention provides a neutralising antibody which binds human IL-17A that binds to an epitope of human IL-17A which comprises or consists of one or more of the residues selected from the group consisting of SER41, ASN52, ARG72, HIS73 and ASP84 of human IL-17A (SEQ ID NO:21).

In one embodiment, the present invention provides a neutralising antibody which binds human IL-17A that binds to an epitope of human IL-17A which comprises or consists of one or more of the residues selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:21).

In one embodiment an antibody of the present invention does not bind one or more e.g two or more of the amino acid residues selected from the group consisting of ASP80, GLY81 and ASN82 of human IL-17A (SEQ ID NO:21).

In one embodiment an antibody of the present invention does not bind one or more amino acid residues selected from the group consisting of ASP80, GLY81, ASN82 and VAL83 of human IL-17A (SEQ ID NO:21).

In one embodiment an antibody of the present invention does not bind any of the following amino acid residues, ASP80, GLY81 and ASN82 of human IL-17A (SEQ ID NO:21).

In one embodiment the invention provides antibodies which bind to, and/or interact with, a neutralising epitope of IL-17F provided by the present invention.

Accordingly, in one embodiment the present invention provides a neutralising antibody which binds human IL-17F that binds to an epitope of human IL-17F comprising one or more e.g. three or more, e.g. five or more, e.g. ten or more of the following residues: SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128 of SEQ ID NO:22 (IL-17F).

In one embodiment the present invention provides a neutralising antibody which binds human IL-17F that binds to an epitope of human IL-17F within one or more of the following regions:

(i) 39-42 (SER39, MET40, SER41, ARG42)
(ii) 47 (ARG47)
(iii) 53 (ASN53)
(iv) 72-75 (CYS72, ARG73, ASN74, LEU75)
(v) 83-92 (LYS83, GLU84, ASP85, ILE86, SER87, MET88, ASN89, SER90, VAL91, PRO92)
(vi) 94 (GLN94)
(vii) 119 (THR119)
(viii) 122 (CYS122)
(ix) 125-128 (VAL125, THR126, PRO127, VAL128).

In one embodiment an antibody of the present invention binds human IL-17A and human IL-17F.

In one embodiment an antibody of the present invention binds human IL-17A/F heterodimer.

In one embodiment, an antibody of the present invention binds human IL-17A and human IL-17A/F heterodimer. In one embodiment an antibody of the present invention binds human IL-17F and human IL-17A/F heterodimer. In a preferred embodiment, an antibody of the present invention binds human IL-17A, human IL-17F and human IL-17A/F heterodimer.

Accordingly, in one embodiment the present invention provides a neutralising antibody which binds human IL-17A and human IL-17F that binds to an epitope of human IL-17A comprising one or more of the residues selected from the group consisting of TYR44, ASN45, TRP51, ASN52 and ASP84 of SEQ ID NO:21 (IL-17A) wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and human IL-17F that binds to an epitope of human IL-17A comprising ASN52 and ASP84 of SEQ ID NO:21 (IL-17A) and optionally one or more amino acid residues selected from the group consisting of SER41, TYR44, ASN45, ARG46, TRP51, HIS54, ARG72, HIS73, HIS86, VAL128, HIS129 and VAL131 wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and IL-17F that binds to an epitope of human IL-17F comprising one or more of the amino acid residues selected from the group consisting of SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127 and VAL128 of human IL-17F (SEQ ID NO:22) wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and IL-17F that binds to an epitope of human IL-17F within one or more of the following regions:
(i) 39-42 (SER39, MET40, SER41, ARG42)
(ii) 47 (ARG47)
(iii) 53 (ASN53)
(iv) 72-75 (CYS72, ARG73, ASN74, LEU75)
(v) 83-92 (LYS83, GLU84, ASP85, ILE86, SER87, MET88, ASN89, SER90, VAL91, PRO92)
(vi) 94 (GLN94)
(vii) 119 (THR119)
(viii) 122 (CYS 122)
(ix) 125-128 (VAL125, THR126, PRO127, VAL128).
wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment the present invention provides a neutralising antibody which binds human IL-17A and IL-17F that binds to an epitope of human IL-17A comprising one or more of the amino acids selected from the group consisting of SER41, TYR44, ASN45, ARG46, TRP51, ASN52, HIS54, ARG72, HIS73, ASP84, HIS86, VAL128, HIS129 and VAL131 of human IL-17A (SEQ ID NO:21) and that binds to an epitope of human IL-17F comprising one or more of the amino acid residues selected from the group consisting of SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127 and VAL128 of human IL-17F (SEQ ID NO:22) wherein the antibody is not an antibody comprising the sequence given in SEQ ID NO:1 for CDR-H1, the sequence given in SEQ ID NO:2 for CDR-H2, the sequence given in SEQ ID NO:3 for CDR-H3, the sequence given in SEQ ID NO:4 for CDR-L1, the sequence given in SEQ ID NO:5 for CDR-L2 and the sequence given in SEQ ID NO:6 for CDR-L3.

In one embodiment an antibody of the present invention which is capable of binding to both IL-17A and IL-17F is capable of neutralising the activity of both isoforms of IL-17. In particular, in one embodiment an antibody of the present invention is capable of specifically binding to both IL-17A and IL-17F i.e. the antibody does not bind to other isoforms of IL-17. Preferably an antibody of the present invention also binds the IL-17A/IL-17F heterodimer. Preferably, an antibody of the present invention neutralises the activity of both IL-17A and IL-17F. In one embodiment an antibody of the present invention also neutralises the activity of the IL-17A/IL-17F heterodimer. The antibodies provided by this aspect of the present invention therefore have the advantageous property that they can inhibit the biological activity of both IL-17A and IL-17F. Accordingly, the present invention also provides the use of such antibodies in the treatment of and/or prophylaxis of a disease mediated by either or both of IL-17A or IL-17F such as autoimmune or inflammatory disease or cancer.

IL-17A or IL-17F polypeptides or a mixture of the two or cells expressing one or both of said polypeptides can be used to produce antibodies which specifically recognise one or both polypeptides. The IL-17 polypeptides (IL-17A and IL-17F) may be 'mature' polypeptides or biologically active fragments or derivatives thereof which preferably include the receptor binding site. Preferably the IL-17 polypeptides are the mature polypeptides provided in SEQ ID NOs 21 and 22 for IL-17A and IL-17F respectively. IL-17 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-17 polypeptide may in some instances be part of a larger protein such as a fusion protein for example fused to an affinity tag. Antibodies generated against these polypeptides may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows or pigs may be immunized. However, mice, rabbits, pigs and rats are generally preferred.

Antibodies for use in the present invention include whole antibodies and functionally active fragments or derivatives thereof and may be, but are not limited to, monoclonal, multivalent, multi-specific, fully human, humanized or chimeric antibodies, domain antibodies e.g. VH, VL, VHH, single chain antibodies, Fab fragments, Fab' and F(ab')$_2$ fragments and epitope-binding fragments of any of the above. Other antibody fragments include those described in International patent applications WO2005003169, WO2005003170 and WO2005003171. Antibody fragments and methods of producing them are well known in the art, see for example Verma et al., 1998, Journal of Immunological Methods, 216, 165-181; Adair and Lawson, 2005. Therapeutic antibodies. *Drug Design Reviews-Online* 2(3):209-217.

Antibodies for use in the present invention include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule. The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-17 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. Particularly preferred is the IgG4 constant domain comprising this change. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Humanized antibodies are antibody molecules from non-human species having one or more complementarity determining regions (CDRs) from the non-human species and a framework region from a human immunoglobulin molecule (see, e.g. U.S. Pat. No. 5,585,089; WO91/09967).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multivalent antibodies may comprise multiple specificities or may be monospecific (see for example WO 92/22853 and WO05/113605).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies which bind to IL-17A and IL-17F. Also, transgenic mice, or other organisms, including other mammals, may be used to express humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

Any suitable method known in the art may be used to determine the residues bound by an antibody provided by the present invention e.g. hydrogen-deuterium exchange, site-directed mutagenesis, mass spectrometry, NMR and X-ray crystallography. See for example the methods described in WO2007/149032.

The specific region or epitope of the human IL-17A polypeptide and/or the specific region or epitope of the human IL-17F polypeptide and/or the specific region or epitope of the human IL-17A/F heterodimer can be identified by any suitable epitope mapping method known in the art in combination with any one of the antibodies provided by the present invention. Examples of such methods include screening peptides of varying lengths derived from IL-17A and IL-17F for binding to the antibody of the present invention with the smallest fragment that can specifically bind to the antibody containing the sequence of the epitope recognised by the antibody. The IL-17 peptides may be produced synthetically or by proteolytic digestion of the appropriate IL-17 polypeptide. Peptides that bind the antibody can be identified by, for example, mass spectrometric analysis. In another example, NMR spectroscopy, as described in the Examples herein can be used to identify residues which interact with an antibody of the present invention.

The neutralising antibody molecules provided by the present invention preferably have a high binding affinity, preferably nanomolar, even more preferably picomolar. It will be appreciated that the binding affinity of an antibody according to the present invention for human IL-17A may be different from the binding affinity of the same antibody for human IL-17F and/or the IL-17A/F heterodimer. In one example the antibody molecule of the present invention has an affinity for IL-17A that is greater than its affinity for IL-17F. In one example the antibody molecule of the present invention has an affinity for IL-17A which is at least 10 fold greater than its binding affinity for IL-17F. In one example the antibody molecule of the present invention has an affinity for IL-17A which is at least 50 fold greater than its binding affinity for IL-17F. In one example the antibody molecule of the present invention has an affinity for IL-17A which is at least 100 fold greater than its binding affinity for IL-17F. In one example the antibody molecule of the present invention has an affinity for IL-17F that is greater than its affinity for IL-17A. In one example the antibody molecule of the present invention has an affinity for IL-17A that is the same as its affinity for IL-17F. In one example the antibody molecule of the present invention has a picomolar affinity for IL-17A and a nanomolar affinity for IL-17F. In one example the antibody molecule of the present invention has a nanomolar affinity for IL-17F and a picomolar affinity for IL-17A. In one example the antibody molecule of the present invention has a nanomolar affinity for both IL-17A and IL-17F. In one example the antibody molecule of the present invention has a picomolar affinity for both IL-17A and IL-17F.

Preferably the antibody molecule of the present invention has a binding affinity for IL-17A of better than 10 nM. In one embodiment the antibody molecule of the present invention has a binding affinity for IL-17A of better than 500 pM. In one embodiment the antibody molecule of the present invention has a binding affinity for IL-17A of better than 100 pM. In one embodiment the antibody molecule of the present invention has a binding affinity for IL-17A of better than 20 pM.

Preferably the antibody molecule of the present invention has a binding affinity for IL-17F of better than 10 nM. In one embodiment the antibody of the present invention has an affinity for IL-17F of better than 2 nM. In one embodiment the antibody of the present invention has an affinity for IL-17F of better than 500 pM. In one embodiment the antibody molecule of the present invention has a binding affinity for IL-17F of better than 100 pM.

Preferably the antibody molecule of the present invention has a binding affinity for IL-17A/F heterodimer of better than 10 nM. In one embodiment the antibody molecule of the present invention has a binding affinity for IL-17A/F heterodimer of better than 500 pM. In one embodiment the antibody molecule of the present invention has a binding affinity for IL-17A/F heterodimer of better than 100 pM.

In one embodiment the antibody molecule of the present invention has a binding affinity for cynomolgus IL-17F of better than 2 nM.

It will be appreciated that the affinity of antibodies provided by the present invention may be altered using any suitable method known in the art. The present invention therefore also relates to variants of the antibody molecules of the present invention, which have an improved affinity for IL-17A and/or IL-17F. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention neutralise IL-17A and IL-17F activity, for example in the in vitro assays described in the Examples. In one embodiment the present invention provides a neutralising antibody having specificity for human IL-17A and IL-17F which is capable of inhibiting the activity of 0.8 nM human IL-17A by 50% at a concentration of less than 5 nM and the activity of 4.2 nM IL-17F by 50% at a concentration of less than 12 nM said inhibitory activity being measured on the IL-17A or IL-17F induced release of IL-6 from Hela cells. In one embodiment the concentration of antibody which inhibits IL-17A by 50% is less than 3 nM. In one embodiment the concentration of antibody which inhibits IL-17F by 50% is less than 11 nM. In one embodiment the human IL-17A and human IL-17F used in the assay are recombinant human IL-17A and IL-17F. In one embodiment the neutralising antibody is a humanised or fully human antibody.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups.

Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO98/25971). In one example the antibody molecule of the present invention is a modified Fab fragment wherein the modification is the addition to the C-terminal end of its heavy chain one or more amino acids to allow the attachment of an effector molecule. Preferably, the additional amino acids form a modified hinge region containing one or more cysteine residues to which the effector molecule may be attached. Multiple sites can be used to attach two or more PEG molecules.

Preferably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

In one embodiment, the antibody is a modified Fab fragment which is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly (ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, a neutralising antibody molecule of the present invention is a modified Fab fragment having at the C-terminal end of its heavy chain a modified hinge region containing at least one cysteine residue to which an effector molecule is attached. Preferably the effector molecule is PEG and is attached using the methods described in (WO98/25971 and WO2004072116) whereby a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da.

In another example effector molecules may be attached to antibody fragments using the methods described in International patent applications WO2005/003169, WO2005/003170 and WO2005/003171.

The present invention also provides an isolated DNA sequence encoding the heavy and/or light chain(s) of an antibody molecule of the present invention. Preferably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

The present invention also relates to a cloning or expression vector comprising one or more DNA sequences of the present invention. Accordingly, provided is a cloning or expression vector comprising one or more DNA sequences encoding an antibody of the present invention. Preferably, the cloning or expression vector comprises two DNA sequences, encoding the light chain and the heavy chain of the antibody molecule of the present invention, respectively.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody according to the present invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines.

The pharmaceutical compositions preferably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, preferably 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Preferred forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, it is preferred that the compositions are adapted for administration to human subjects.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO 98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

It is also envisaged that the antibody of the present invention will be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule for use in the control of inflammatory diseases. Preferably, the antibody molecule can be used to reduce the inflammatory process or to prevent the inflammatory process.

The present invention also provides an antibody molecule of the present invention for use in the treatment or prophylaxis of a pathological disorder that is mediated by IL-17A and/or IL-17F or is associated with an increased level of IL-17A and/or IL-17F. Preferably, the pathological condition is selected from the group consisting of infections (viral, bacterial, fungal and parasitic), endotoxic shock associated with infection, arthritis, rheumatoid arthritis, asthma, pelvic inflammatory disease, Alzheimer's Disease, Crohn's disease, inflammatory bowel disease, Ulcerative colitis, Peyronie's Disease, coeliac disease, gallbladder disease, Pilonidal disease, peritonitis, psoriasis, vasculitis, surgical adhesions, stroke, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, gastric cancer and colon cancer), heart disease including ischaemic diseases such as myocardial infarction as well as atherosclerosis, intravascular coagulation, bone resorption, osteoporosis periodontitis and hypochlorhydia.

The present invention also provides an antibody molecule according to the present invention for use in the treatment or prophylaxis of pain.

The present invention further provides the use of an antibody molecule according to the present invention in the manufacture of a medicament for the treatment or prophylaxis of a pathological disorder that is mediated by IL-17A and/or IL-17F or associated with an increased level of IL-17A and/or IL-17F. Preferably the pathological disorder is rheumatoid arthritis or multiple sclerosis.

The present invention further provides the use of an antibody molecule according to the present invention in the manufacture of a medicament for the treatment or prophylaxis of pain.

An antibody molecule of the present invention may be utilised in any therapy where it is desired to reduce the effects of IL-17A and/or IL-17F in the human or animal body. IL-17 A and/or IL-17F may be circulating in the body or may be present in an undesirably high level localised at a particular site in the body, for example a site of inflammation.

An antibody molecule according to the present invention is preferably used for the control of inflammatory disease, autoimmune disease or cancer.

The present invention also provides a method of treating human or animal subjects suffering from or at risk of a disorder mediated by IL-17A and/or IL-17F, the method comprising administering to the subject an effective amount of an antibody molecule of the present invention.

An antibody molecule according to the present invention may also be used in diagnosis, for example in the in vivo diagnosis and imaging of disease states involving IL-17A and/or IL-17F.

The present invention is further described by way of illustration only in the following examples, which refer to the accompanying Figures, in which: FIG. 1:

a) Light chain V region of antibody CA028_0496 (SEQ ID NO:7)
b) Heavy chain V region of antibody CA028_0496 (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody CA028_496.
d) Light chain of antibody CA028_496 (SEQ ID NO:11).
e) Heavy chain of antibody CA028_496 (SEQ ID NO:15).
f) DNA encoding light chain of antibody CA028_496 including signal sequence (SEQ ID NO:14).
g) DNA encoding heavy chain of antibody CA028_496 including signal sequence (SEQ ID NO:18)
h) Mature human IL-17A.
i) Mature human IL-17F.

Figure 2B:
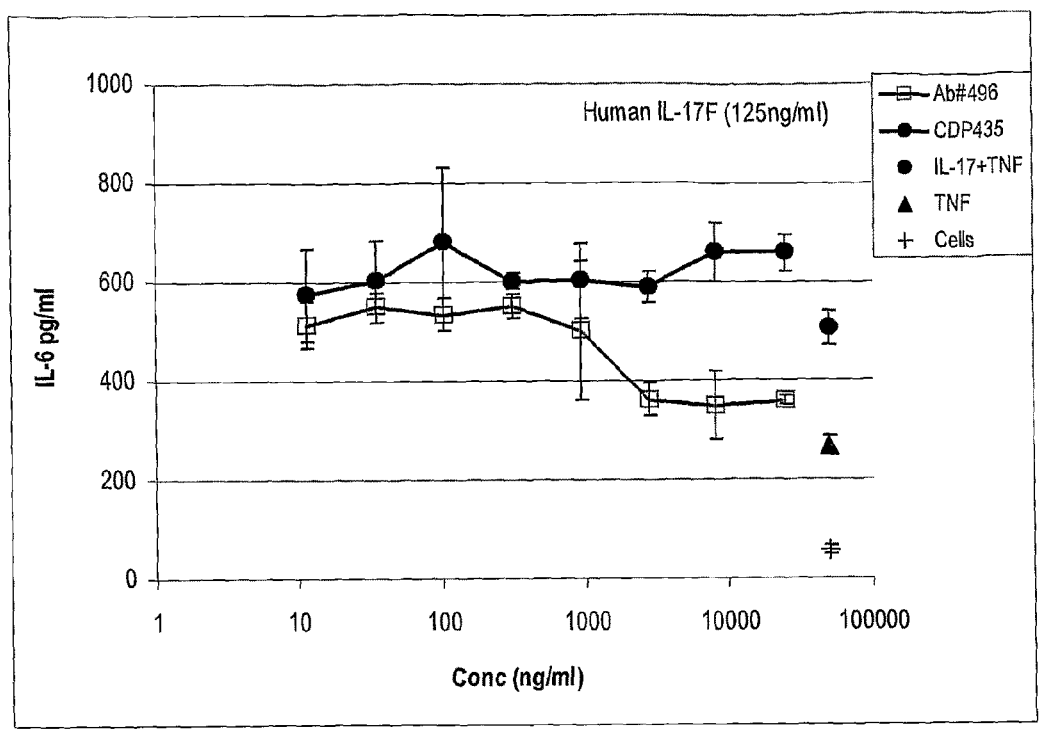

FIG. 2 a) The effect of antibody CA028_0496 (designated Ab#496 in legend) on human IL-17 induced IL-6 production from Hela cells. b) The effect of antibody CA028_0496 (designated Ab#496 in legend) on human IL-17F induced IL-6 production from Hela cells

DNA MANIPULATIONS AND GENERAL METHODS

*E. coli* strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from Invitrogen. The concentration of IgG was determined using IgG assembly ELISA.

IL-17 Isoforms

Recombinant IL-17A and IL-17F were purchased from R&D Systems.

Recombinant IL-17A/F heterodimer was produced by linking IL-17A and IL-17F using a GS linker. The heterodimer had the following sequence (SEQ ID NO:19) MGITIPRNPGCPNSEDKNFPRTVM-VNLNIHNRNTNTNPKRSSDYYNRSTSPWNLHRNE DPERYPSVIWEAKCRHLGCINADGNVDY-HMNSVPIQQEILVLRREPPHCPNSFRLEKIL VSVGCTCVTPIVHH-VAGGGGSGGGGSGGGGSGGGGSRKIP-KVGHTFFQKPESCPPVP GGSMKLDIGIINENQRVSM-SRNIESRSTSPWNYTVTWDPNRYPSEVVQAQCRNLG CIN AQGKEDISMNSVPIQQETLVVR-RKHQGCSVSFQLEKVLVTVGCTCVTPVIHHVQ Recombinant cynomolgus IL-17F (SEQ ID NO:20) MRKIPKVGHTFFQKPESCP-PVPEGSMKLDTGIINENQRVSMSRNI-ESRSTSPWNYTVTWDPNR YPSEVVQAQCKHLGCI-NAQGKEDISMNSVPIQQETLVLRRKHQGCSVSFQLEK VLVTVGCTCV TPVIHHVQ The DNA sequence encoding IL-17A/F heterodimer was chemically synthesised by Entelechon GmbH and was subcloned into pET43.1a at the NdeI/XhoI sites.

The DNA sequence encoding cyno L-17F was amplified by PCR using primers that introduced NdeI and XhoI restriction sites. The PCR products were ligated into pCR4Blunt-TOPO and sequence verified before digestion and ligation into pET43.1a at the NdeI/XhoI sites.

pET43.1a DNA encoding IL-17 isoforms was used to transfect BL21(DE3) cells and selected carbenicillin-resistant clones were grown at 37° C. overnight in 2TY broth containing 2% glucose and 50 µg/ml carbenicillin. The cultures were then diluted and grown in the same medium to an $OD_{600}$ of 0.5-0.7, induced with 1 mM IPTG and grown at 37° C. for a further 4-5 hours.

Cells were harvested by centrifugation and inclusion bodies prepared from from the cells. Inclusion bodies were solubilised in 50 mM Tris-HCl, 5M guanidinium hydrochloride, 50 mM NaCl, 1 mM EDTA, 2 mM reduced glutathione, 0.2 mM oxidised glutathione, pH 8.5. IL-17 protein was refolded by dropwise addition of the solubilised protein to the above buffer without guanidinium hydrochloride, with vigorous stirring. The final volume was chosen such that the final protein concentration was no more than 0.1 mg/ml.

The refolded protein solution was concentrated if required, before buffer exchange with 10 mM MES pH 6. The protein was then applied to a column of Sepharose SP HP equilibrated with 20 mM MES pH 6. Protein was eluted with a linear gradient of 0-500 mM NaCl in MES pH 6 over 10 column volumes. For IL-17F the gradient was extended to 600 mM NaCl. In order to further purify IL-17, the relevant fraction from the Sepharose SP HP column were pooled, concentrated and diluted with 20 mM CAPSO (pH 10) and applied to a Mono Q column equilibrated with 20 mM CAPSO. Protein was eluted with a linear gradient of 0-250 mM NaCl in 20 mM CAPSO over 20 column volumes. Fractions containing IL-17 were pooled and neutralised using 1M MES pH 6.

Example 1

Production of a Neutralising Anti-IL-17 Antibody

Female Sprague Dawly rats were immunised with recombinant human IL-17 (purchased from R & D systems). Rats received four immunisations of 20 µg IL-17 in 100 µl Freund's adjuvant. Antibody 225 which binds human IL-17 was isolated using the methods described in WO04/051268. Genes for the heavy chain variable domain (VH) and light chain variable domain (VL) of antibody 225 were isolated and sequenced following cloning via reverse transcription PCR.

A series of humanised VL and VH regions were designed using human V-region acceptor frameworks and by varying the number of donor residues in the framework regions. Eight grafted VL regions (gL1-8) and 9 grafted VH regions (gH1-9) were designed and genes were built by oligonucleotide assembly and PCR mutagenesis.

The light chain grafted sequences were sub-cloned into the human light chain expression vector pKH10.1 which contains the DNA encoding the human C-Kappa constant region (Km3 allotype). The heavy chain grafted sequences were sub-cloned into the human gamma-4 expression vector pVhg4P FL, which contains the DNA encoding the human gamma-4 constant region containing the hinge stabilising mutation S241P (Angal et al., supra). Plasmids were co-transfected into CHO cells and the antibodies produced screened for activity in IL-17 binding and neutralisation assays. Transfections of CHO cells were performed using the Lipofectamine™ 2000 procedure according to manufacturer's instructions (InVitrogen, catalogue No. 11668).

The most optimal graft based on expression, affinity and neutralisation potency (gL7gH9) was selected and named CA028_0496 (also referred to herein as 496). The V region sequences of this antibody are shown in FIGS. 1 (a) and (b) and in SEQ ID NOs: 7 and 9 for the light chain (gL7) and heavy chains (gH9) respectively.

The heavy chain acceptor framework is the human germline sequence VH3 1-3 3-07 with framework 4 coming from this portion of the human JH-region germline JH4. The light chain acceptor framework is the human germline sequence VK1 2-1-(1) L4, with framework 4 coming from this portion of the human JK-region germline JK1.

Example 2

Antibody CA028_0496 Neutralises IL-17 and IL-17F and IL-17A/F Heterodimer

Hela Cells

The potency of antibody CA028_0496 against human recombinant IL-17 and human recombinant IL-17F in Hela cells was tested and compared to antibody CDP435 (WO06/054059). Hela cells were obtained from the cell bank at ATCC (ATCC CCL-2). Cells were grown in Dulbecco's modified Eagle's medium (DMEM) supplemented with 10% foetal calf serum, penicillin, gentamycin and glutamine. $1 \times 10^4$ cells were plated out into 96 well flat bottomed tissue culture plates. Cells were incubated overnight and washed once in assay buffer. Either human IL-17A (25 ng ml$^{-1}$) or human IL-17F (125 ng ml$^{-1}$) was incubated in the presence of a fixed concentration of human TNF-α this mixture was preincubated with antibody CA028_0496 or antibody CDP435. Cytokine plus antibody was then added to the Hela cells which were incubated overnight. The production of IL-6 in the cell culture supernatant was proportionate to the amount of IL-17A/IL-17F added to the cells. Human IL-6 levels were measured by ELISA and quantified by comparison with known standard concentrations of human IL-6.

The data (FIGS. 2a & 2b) indicates that CA028_0496 potently neutralised human recombinant IL-17A and also had some activity against human IL-17F. The data from these experiments indicated that antibody CA028_0496 gave an $IC_{50}$ of 43 ng/ml against human recombinant IL-17 (25 ng ml$^{-1}$) & 1477 ng/ml against recombinant IL-17F (125 ng ml$^{-1}$). Accordingly, antibody CA028_0496 gave an IC50 of 0.29M against human recombinant IL-17 (0.78 nM) and 10.18 nM against human recombinant IL-17F (4.16 nM) in this assay (calculation based on per IgG assuming a molecular weight of 145,000 as an average IgG4 and assuming that IL-17A and IL-17F are dimers).

Human Microglia Cells

Human microglia cells (TCS Cellworks) were plated out in a flat bottom 96-well plate at 5,000 cells per well in a total volume of 100 µl and left for 24 hours to attach to the plastic. At this time titrations (5, 1, 0.2 and 0.04 µg/ml) of human recombinant IL-17A, human recombinant IL-17F, cynomolgus recombinant IL-17F and human recombinant IL-17A/F heterodimer in the presence and absence of 10 ng/ml human recombinant TNFα were added to wells in triplicate. Control wells contained no stimulation, IL-17A alone (100 ng/ml), TNFα alone and IL-17A and TNFα together. All cytokines were added in a total volume of 110 µl/well, making the total well volume 210 µl. In experiments involving antibodies, cells were plated out in the same way. After 24 hours antibodies and cytokines were added at the same time to give the stated final concentrations in a total final volume of 200 µl.

After a further 24 hours incubation at 37° C., supernatants were harvested and frozen at −20° C. until analysis. For analysis, supernatants were diluted ⅒ and measured for IL-6 using a human IL-6 MSD kit, according to manufacturer's instructions.

All isoforms of IL-17 tested were found to be active in the assay, particularly in the presence of TNFα.

The potency of antibody CA028_0496 against human recombinant IL-17A and human recombinant IL-17F, cynomolgus recombinant IL-17F and human recombinant IL-17A/F heterodimer in human microglia cells was tested in the presence of TNFα and compared to a control antibody and an IL-17A specific antibody using the method described above.

The control antibody had no effect on the activity of any of the cytokines tested. Antibody CA028_0496 had inhibitory activity against all three cytokines IL-17, IL-17F and IL-17A/F, including cynomolgus IL-17F while the IL-17A specific antibody only had inhibitory activity against IL-17A and IL-17A/F heterodimer.

Example 3

Affinity of Antibody CA028_0496 (Human IgG4 Constant Regions) for IL-17A and IL-17F BIA (Biamolecular Interaction Analysis) was performed using a Biacore 3000 (Biacore AB).

All experiments were performed at 25° C. Affinipure Fc Fragment goat anti-human IgG, Fc fragment specific (Jackson ImmunoResearch) was immobilised on a CM5 Sensor Chip via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 µl/min. A 10 µl injection of antibody CA028_0496 (1.81 mg/ml) was used for capture by the immobilised anti-human IgG-Fc. Human IL-17A and IL-17 isoforms were titrated over the captured CA028_0496 at doubling dilutions from 50 nM to sub nM at a flow rate of 30 µL/min. The surface was regenerated by a 30 µL injections of 40 mM HCl, followed by one 5 µL injection of 5 mM NaOH.

Background subtraction binding curves were double referenced and analysed using the BIAevaluation software (version 3.2) following standard procedures. Kinetic parameters were determined from the fitting algorithm.

The affinity value determined for antibody CA028_0496 binding IL-17A was 16 pM and 1750 pM for IL-17F. Antibody CA028_0496 did not bind to the other IL-17 isoforms (IL-17 B, C, D and E). Antibody CA028_0496 therefore specifically binds IL-17A and IL-17F.

Example 4

Affinity of Antibody CA028_0496 (Murine IgG1 Constant Regions) for IL-17A, Cynomolgus IL-17F and IL-17A/F Heterodimer BIA (Biamolecular Interaction Analysis) was performed using a Biacore 3000 (Biacore AB).

All experiments were performed at 25° C. Affinipure F(ab')$_2$ fragment goat anti-mouse IgG, Fc fragment specific (Jackson ImmunoResearch) was immobilised on a CM5 Sensor Chip (Biacore AB) via amine coupling chemistry to a capture level of ≈6000 response units (RUs). HBS-EP buffer (10 mM HEPES pH 7.4, 0.15 M NaCl, 3 mM EDTA, 0.005% Surfactant P20, Biacore AB) was used as the running buffer with a flow rate of 10 μL/min. A 10 μL injection of antibody CA028_0496 at 4 ug/mlL was used for capture by the immobilised anti-mouse IgG, Fc. Human IL-17A, cyno IL-17F and heterodimerA/F were titrated over the captured CA028_0496 at doubling dilutions from 25 nM to sub nM at a flow rate of 30 μL/min. The surface was regenerated at a flowrate of 10 uL/min by a 10 μL injection of 40 mM HCl, followed by a 5 μL injection of 5 mM NaOH.

Double referenced background subtracted binding curves were analysed using the BIAevaluation software (version 3.2) following standard procedures. Kinetic parameters were determined from the fitting algorithm.

Antibody CA028_0496 had an affinity of 21 pM for IL-17A, 116 pM for IL-17A/F heterodimer and 1030 pM for cynomolgus IL-17F.

Example 5

Epitope Mapping by NMR of a Fab' Fragment Comprising the Variable Regions of Antibody CA028_0496

Antibody CA028_0496 was produced as a Fab' fragment comprising '496 variable regions and murine IgG1 constant regions (SEQ ID NO:23 and 24).

```
Heavy chain sequence
                                                  (SEQ ID NO: 23)
EVQLVESGGG LVQPGGSLRL SCAASGFTFS DYNMAWVRQA

PGKGLEWVAT ITYEGRNTYY RDSVKGRFTI SRDNAKNSLY

LQMNSLRAED TAVYYCASPP QYYEGSIYRL WFAHWGQGTL

VTVSSAKTTP PSVYPLAPGS AAQTNSMVTL GCLVKGYFPE

PVTVTWNSGS LSSGVHTFPA VLQSDLYTLS SSVTVPSSTW

PSETVTCNVA HPASSTKVDK KIVPRDCGCA AAIQLTQSPS

SLSASVGDRV TITCRADESV TTLMHWYQQK PGKAPKLLIY

LVSNRESGVP SRFSGSGSGT DFTLTISSLQ PEDFATYYCQ

QTWSDPWTFG QGTKVEIKRT DAAPTVSIFP PSSEQLTSGG

ASVVCFLNNF YPKDINVKWK IDGSERQNGV LNSWTDQDSK

DSTYSMSSTL TLTKDEYERH NSYTCEATHK TSTSPIVKSF NRNEC

Light chain sequence
                                                  (SEQ ID NO: 24)
AIQLTQSPSS LSASVGDRVT ITCRADESVT TLMHWYQQKP

GKAPKLLIYL VSNRESGVPS RFSGSGSGTD FTLTISSLQP

EDFATYYCQQ TWSDPWTFGQ GTKVEIK
```

Transient Expression of CA028_00496.g1 mFab' in a 10 L Wave Bioreactor

For the transfection of the HEK 293 F cells in a 10 L wave bag, 10 L of the in-house NM6 medium was prepared and supplemented with 2 mM Glutamax (Invitrogen). The cells were counted and seeded into the bag at a final cell density of 10×10$^6$ cells/ml. The transfection mixture was prepared in 700 ml of NM6 medium. For the preparation of the transfection mixture the NM6 medium was divided into two halves. To one half 5 mg of the heavy chain plasmid DNA and 5 mg of the light chain plasmid DNA was added and gently shaken. To the other half 37 ml of a 1 mg/ml linear 25 kD polyethylenimine (PEI) stock solution was added and gently shaken. Thereafter NM6 medium containing the DNA was slowly transferred to the NM6 medium containing the PEI. The mixture was incubated at room temperature for 20 minutes before added to the cell suspension in the wave bag. The transfected cells were cultured over 14 days at 25 rpm, a 7° angle, 37° C. and 5% CO2. Samples were taken regularly to determine the cell density and viability. On day 14 post transfection cells were harvested. The 10 L cell suspension was transferred to centrifuge bottles and spun at 4000 rpm for 45 min. The supernatant was then passed through a Sartobran (0.45 μm to 0.2 μm) filter and finally through a Millipack Gold60 (0.22 μm) sterile filter. Fab' was then purified from the sterile filtered supernatant.

Purification of CA028_00496.g1 mFab'

Transiently expressed CA028_00496.g1 mFab' was purified from mammalian host cells (HEK293F) as follows. The mammalian host cell conditioned medium containing secreted CA028_00496.g1 mFab' was concentrated 10 fold by tangential flow ultrafiltration (TFF) using a 10,000 MWCO membrane. The concentrated supernatant was passed down a GammaBind Plus Sepharose column (media supplied by GE Healthcare) which had been equilibrated with 75 mM citrate/phosphate buffer, pH 6.0. After loading, the GammaBind Plus Sepharose column was washed with 75 mM citrate/phosphate buffer, pH 6.0 until the absorbance at 280 nm of the flow-through returned to baseline. The CA028_00496.g1 mFab' was then eluted from the column by stepping into 0.1M glycine-HCl buffer, pH 2.7. The absorbance at 280 nm of the eluate was monitored and fractions containing protein were collected. Supernatant loading and column elution were performed in two batches so as not to exceed the capacity of the column.

Fractions containing protein were combined and buffer exchanged (by diafiltration) into 0.1M sodium phosphate buffer, pH 6.0+2 mM EDTA using an Amicon stirred cell and 10,000 MWCO membrane. The affinity purified CA028_00496.g1 mFab' was concentrated to 20 mg/ml prior to reduction. Disulphide bonded cysteines at the hinge region were reduced by incubating the Fab' with 5 mM β-Mercaptoethylamine at 37° C. for 30 minutes. The reduction was stopped by adding 50 mM N-Ethylmaleimide (NEM) to cap the reduced thiol groups. The capping reaction was incubated at +4° C. overnight. Excess capping agent and high molecular weight impurities were removed by preparative Gel Filtration. The reduced and capped Fab' was loaded onto a Superdex 200 column (GE Healthcare) and eluted in PBS, pH 7.4. The absorbance at 280 nm of the eluate was monitored and fractions containing protein were collected. Fractions were analysed for purity by analytical SE-HPLC using a Zorbax GF250 column (Agilent) run in 0.2M sodium phosphate buffer, pH 7.0. Fractions containing pure Fab' were combined, 0.22 µm sterile filtered and stored at +4° C. Final purity was analysed by SE-HPLC (as above) and non-reducing and reducing SDS-PAGE.

Preparation of dN- and dCN-labelled hIL17A

The DNA sequence encoding IL-17A was amplified by PCR using primers that introduced NdeI and XhoI restriction sites. The PCR products were ligated into pCR4Blunt-TOPO and sequence verified before digestion and ligation into pET43.1 a at the NdeI/XhoI sites.

hIL17A-pET43.1a was used to transform *E. coli* strain BL21(DE3). 1 ml of LB inoculated with transformed cells. Cells incubated overnight at 37° C. Dense overnight culture used to inoculate 30% dN labelled Celltone media at 1:40 dilution. Cells incubated overnight at 37° C. Dense overnight culture then used to inoculate 30% dN- or dCN-labelled Celltone media. Culture incubated overnight at 37° C. This step was then repeated with 70% media and then finally with 100% media. 100% dN- or dCN-labelled media inoculated with dense overnight culture and grown to 0.8 OD 595 nm. Culture induced with a final concentration 1 mM IPTG and incubated for 6 hours at 37° C. Cells harvested by centrifugation.

Inclusion Bodies Extracted (for 2 L of Culture).

1) Resuspend cell pellet in 40 ml Buffer A (100 mM KCl, 2 mM DTT, 2 mM PMSF, 10 mM Tris-HCl pH 8.5, 25% (w/v) sucrose)
2) Add 10 ml Buffer B (300 mM Tris-HCl pH 8.5, 100 mM EDTA, 4 mg/ml lysozyme) Incubate on ice for 10-30 minutes with occasional swirling.
3) Add 50 ml Buffer C (1M LiCl, 20 mM EDTA, 0.5% (v/v) NP-40). Sonicate sample to homogenise. Pass sample through French Press at 20,000 psi. Pass sample through French Press again. Spin sample at 10,000 rpm for 10 minutes @ 4° C.
4) Resuspend pellet in 40 ml Buffer D (10 mM Tris-HCl pH 8.5, 0.1 mM EDTA, 0.5M LiCl, 0.5% (v/v) NP-40, 1 mM DTT, 1 mM PMSF). Sonicate to homogenise and spin at 10,000 rpm for 10 minutes @ 4° C. Repeat step.
5) Resuspend pellet in 40 ml Buffer E (10 mM Tris-HCl pH 8.5, 0.1 mM EDTA, 0.5% (v/v) NP-40, 1 mM DTT, 1 mM PMSF). Sonicate to homogenise and spin at 10,000 rpm for 10 minutes @ 4° C. Repeat step.

Resolubilisation of Pellet

6) Make up 6M Guanidine HCl, 50 mM Tris-HCl pH 8.5, 50 mM NaCl. Add to pellet. Stir pellet until completely dissolved.
7) Filter sample through a 0.2 uM syringe filter.

Refolding and Dialysis 1) 2.5 ml resolubilised inclusion bodies diluted into 50 ml of 5M Guanidine-HCl, 50 mM Tris pH 8.5, 50 mM NaCl, 1 mM EDTA, 2 mM reduced-Glutathione, 0.2 mM oxidised-Glutathione.
2) Diluted inclusion bodies added drop wise to 500 ml of 50 mM Tris pH 8.5, 50 mM NaCl, 1 mM EDTA, 2 mM reduced-Glutathione, 0.2 mM oxidised-Glutathione.
3) Refolded protein dialyse against 20 mM MES pH 6 overnight at 4° C.

Purification of Labelled Protein

1) Dialysed lysate loaded onto a Mono SP HP (cation) column equilibrated with 20 mM MES pH 6
2) Protein eluted with 50% NaCl gradient over 10 column volumes.
3) Eluted protein buffer exchanged into 20 mM NaPi, 100 mM NaCl, 0.02% azide pH 6 and concentrated and assayed for concentration.

Purification of Unlabelled Protein

1) Dialysed lysate loaded onto a Mono SP HP (cation) column equilibrated with 20 mM MES pH 6.
2) Protein eluted with 50% gradient of 1M NaCl over 10 column volumes.
3) Eluted protein concentrated and buffer exchanged into 20 mM CAPSO buffer pH 10 and loaded onto a MonoQ column equilibrated with 20 mM CAPSO buffer pH 10.
4) Protein eluted with 50% gradient of 1M NaCl over 20 column volumes.
5) Eluted protein concentrated.
6) Concentrated protein injected onto a Superdex 75 16?60 column for a final polishing step. Column equilibrated with 20 mM HEPES, 50 mM NaCl pH 7.4. Eluted protein collected and concentrated and assayed for concentration.

Principle of the NMR Epitope Mapping Assay

The NMR technology allows the sensitive detection of changes in the environment of paramagnetic species. In practice this means that a protein that has been uniformly $^{15}$N and $^{2}$H labelled can be mixed with an unlabelled binding partner and those amino acids in the labelled protein that interact with the unlabelled binding partner can be detected as their position within the NMR spectra change. In this case, human IL-17A was uniformly labelled and its NMR spectra recorded in the presence and absence of the Fab' fragment of an anti-IL-17A antibody. The difference between the two spectra enables the amino acids in IL-17A that are involved in the interaction with the antibody to be identified.

NMR Spectroscopy

The NMR experiments were carried out on 0.35 mL samples of the proteins and complexes in a 25 mM sodium phosphate, 100 mM sodium chloride and 0.01% (w/v) sodium azide buffer at pH 6 (95% $H_2O$ and 5% $D_2O$). The 1:2 (dimer:Fab) complex between $^{15}$N/$^{2}$H labelled IL-17A and the unlabelled Fab' fragment of antibody '496 was prepared for NMR analysis by mixing equimolar (monomer:Fab) amounts of the proteins to achieve a final concentration of 0.25 mM. The NMR data were acquired at 35° C. for free IL-17A and for the IL-17A:Fab' fragment of '496 complex on a 800 MHz Bruker Avance spectrometer equipped with a triple-resonance ($^{15}$N/$^{13}$C/$^{1}$H) cryoprobe. TROSY-based HNCACB, HN(CO)CACB and HNCO spectra (1-4) were used to make complete sequence-specific backbone resonance assignments ($^{15}$N, $^{13}$C and $^{1}$H) for free IL-17A using a 0.8 mM uniformly $^{15}$N/$^{13}$C labelled sample.

Changes in the positions of IL-17A backbone signals induced by the Fab' fragment of '496 binding were detected using a 2D $^{15}$N/$^{1}$H TROSY spectrum (5). Typical acquisition parameters for all the NMR experiments are set out below.

Basic parameters of NMR experiments.

| Experiment | Indirect dimension | Sweep width [ppm] | Carrier offset [ppm] | Acquisition time [ms] |
|---|---|---|---|---|
| TROSY-HNCACB & | $^{15}$N (F2) | 32 | 118.0 | 19.3 |
| TROSY-HN(CO)CACB | $^{13}$C (F1) | 56 | 44.0 | 8.0 |
| TROSY-HNCO | $^{15}$N (F2) | 32 | 118.5 | 20.6 |
| | $^{13}$C (F1) | 11.5 | 175.5 | 24.8 |
| 2D $^{15}$N/$^1$H HSQC | $^{15}$N (F1) | 34 | 118.0 | 80 |
| 2D $^{15}$N/$^1$H TROSY | $^{15}$N (F1) | 34 | 117.5 | 50 |

The direct $^1$H dimension (F3 or F2) was acquired with a sweep width of 14 ppm and acquisition time of 90 or 60 ms.

All the spectra were processed using Topspin 2.1, with linear prediction used to extend the effective acquisition time in the $^{15}$N dimension of 3D data to about 30 ms. Mild resolution enhancement was applied in all dimensions using a shifted sine-squared function. Analysis of the spectra was carried out using Sparky (7).

Analysis of Fab' Binding Data

The minimal shift approach (Farmer, B. T. et al., (1996) *Nat Struct Mol Biol* 3(12), 995; Muskett, F. W. et al., (1998) *J Biol Chem* 273(34), 21736-21743) was used to determine the changes in the positions of IL-17A NMR signals resulting from the Fab' fragment of '496 binding to human IL-17A. Initially, all peaks in the 2D $^{15}$N/$^1$H HSQC spectrum of free IL-17A and 2D $^{15}$N/$^1$H TROSY spectrum of IL-17A bound to the Fab' fragment of '496 were picked in their centres. The $^{15}$N and $^1$H chemical shift values of backbone resonances were corrected for the difference in the 2D $^{15}$N/$^1$H TROSY and 2D $^{15}$N/$^1$H HSQC spectra of the complex and free protein (0.58 ppm for $^{15}$N and −0.06 ppm for $^1$H). The minimum change in position for peaks between free and Fab'-bound IL-17A was obtained by using Microsoft Excel to calculate the combined chemical shift difference in $^{15}$N and $^1$H for each assigned peak in the $^{15}$N/$^1$H HSQC spectrum of the free protein compared to all observed peaks in $^{15}$N/$^1$H TROSY spectrum of the Fab' complex. The combined amide proton and nitrogen chemical shift differences (Δδ) were defined according to the following equation (Equation 1), where $\Delta\delta_{HN}$ and $\Delta\delta_N$ correspond to the differences in $^1$H and $^{15}$N shifts between pairs of compared peaks and $\alpha_N$ is a scaling factor of 0.2 required to account for differences in the range of amide proton, amide nitrogen and carbon chemical shifts. For each individual peak, the minimal shift induced by Fab' binding was taken as the lowest possible combined shift value (Δδ).

$$\Delta\delta = \sqrt{(\Delta\delta_{HN})^2 + (\Delta\delta_N \cdot \alpha_N)^2} \quad \text{(Equation 1)}$$

To identify the Fab' binding sites (epitopes) on IL-17A, a histogram of combined minimal shift versus protein sequence was used to reveal regions of IL-17A containing significantly perturbed signals. If the size of the combined chemical shift change for individual amino acids exceeded a threshold value, these residues were selected for further evaluation as possible contact residues in the Fab' binding site. It will be appreciated that these possible 'contact' residues may be involved in binding by direct or indirect (e.g. allosteric) interactions with the Fab'. The threshold values were set as +1.5× SD of all the minimal shift data, the mean minimal shift +1 SD and the mean minimal shift +2 SD. The locations of candidate binding site residues were finally examined on the high resolution structure of IL-17A and only residues positioned on the protein surface were considered to be available for Fab' binding.

Residues selected as possible 'contact' residues based on shifts>+1.5×SD of all the minimal shift data, solvent accessibility>25%:
SER41, TYR44, ASN45, ARG46, TRP51, ASN52, HIS54, ARG72, HIS73, ASP84, HIS86, VAL128, HIS129 and VAL131.

Residues selected as possible 'contact' residues based on shifts>the mean+1 SD of all minimal shift data, solvent accessibility>25%:
SER41, TYR44, ASN45, TRP51, ASN52, HIS54, ARG72, HIS73 and ASP84.

Residues selected as possible 'contact' residues based on shifts>the mean+2 SD of all minimal shift data, solvent accessibility>25%:
TYR44, ASN45, TRP51, ASN52 and ASP84.

The NMR technique described above was also used to identify the Fab' binding sites (epitopes) on IL-17F.

The threshold values were set as the mean minimal shift, the mean minimal shift +0.5 SD and the mean minimal shift +1 SD. The locations of candidate binding site residues were finally examined on the high resolution structure of IL-17F and only residues positioned on the protein surface were considered to be available for Fab' binding.

Residues selected as possible 'contact' residues based on shifts>mean of all the minimal shift data, solvent accessibility>20%:
GLN12, LYS13, SER24, ISO32, ASN33 GLU34, ASN35, GLN36, VAL38, SER46, ASN53, TYR54, GLN69, ISO78, ASP85, SER87, MET88, ASM89, GLN94, LYS103 and THR126.

Residues selected as possible 'contact' residues based on shifts>the mean+0.5 SD of all minimal shift data, solvent accessibility>20%:
GLN12, SER24, ASN33, GLU34, GLN36, VAL38, ASN53, TYR54, ASP85, MET88, ASM89, and THR126.

Residues selected as possible 'contact' residues based on shifts>the mean+1 SD of all minimal shift data, solvent accessibility>20%:
GLN12, SER24, ASN33, GLU34, ASP85 and MET88.

Example 6

Modelling of Antibody 496 Binding on IL-17F

The probable binding site for antibody 496 on human IL-17F was determined by homology modelling and docking.

MODELLER (Sali, A. & Blundell, T. L., (1993) *J. Mol. Biol.* 234(3), 779-815) was used to build a homology model of antibody 496, using the x-ray structure of antibody CA048_497 (antibody described in WO2008/001063). The overall sequence identity between the two antibodies is 82%. At such high similarity level, the homology modelling process is well understood by anyone who is skilled in the art.

The homology model of antibody 496 was then docked to the x-ray structure of IL17A/F heterodimer using RosettaDock (Gray, J. J., et. al., (2003) *J. Mol. Biol.*, 331(1), 281-299) in order to build a 3D model of the complex. A global unrestricted docking process was carried out to generate 10,000 decoys (i.e., potential docking solutions). The top 10 decoys with lowest energy scores, according to RosettaDock, were selected for perturbation study to probe the energy landscape around each docking solution. The perturbation studies were again carried out using RosettaDock. Decoys that had funnel-like energy landscape were promoted as potential candidates.

The potential candidates were then screened against proximity to residues ASP80, GLY81 and ASN82 of the IL17A subunit and to residues GLN81, GLY82 and LYS83 of the IL17F subunit. Candidates that had antibody 496 located within 4 angstroms from any of such residues were discarded. Note that residues ASP80, GLY81 and ASN82 of IL17A, which are structurally equivalent to residues GLN81, GLY82 and LYS83 of IL17F, were not identified as possible contact residues by the minimal shift data as shown in Example 5, but were identified as possible contact residues when the binding of antibody CA048_497 and IL17A was studied using the same technique (data not shown).

The remaining candidates were then screened for proximity to IL17F residues ARG42, GLU45, SER46, ARG47, TRP52, ASN53, THR55, ARG73, ASN74, LEU75, ASP85 and SER87 ("IL17F-496 Key Residues"), which are structurally equivalent to the possible IL17A contact residues specified in Example 5. Note that the residues that are structurally equivalent to VAL128, HIS129 and VAL131 of IL17A are not present in the x-ray structure IL17F and thus ignored. The candidate with the lowest sum of distances between "IL17F-496 Key Residues" and antibody 496 was selected as the final docking solution.

The proximity screening protocols were carried out using PyMol (DeLano, W. L. The PyMOL Molecular Graphics System (2002) on World Wide Web http://www.pymol.org). According to the final docking solution, antibody 496 is expected to bind IL-17F at one or more of the following residues:

SER39, MET40, SER41, ARG42, ARG47, ASN53, CYS72, ARG73, ASN74, LEU75, LYS83, GLU84, ASP85, ILE86, SER87, MET88, ASN89, SER90, VAL91, PRO92, GLN94, THR119, CYS122, VAL125, THR126, PRO127, VAL128.

Antibody 496 is expected to bind within one or more of the following regions, comprising amino acid residues:

39-42 (SER39, MET40, SER41, ARG42)
47 (ARG47)
53 (ASN53)
72-75 (CYS72, ARG73, ASN74, LEU75)
83-92 (LYS83, GLU84, ASP85, ILE86, SER87, MET88, ASN89, SER90, VAL91, PRO92)
94 (GLN94)
119 (THR119)
122 (CYS122)
125-128 (VAL125, THR126, PRO127, VAL128).

Note that CYS72, SER90, THR119, CYS122 and VAL125 are less than 25% solvent accessible, according to the x-ray structure of IL17F, thus may not directly interact with antibody 496. These residues, however, are likely to support surrounding residues that are making direct contacts with antibody 496.

Therefore antibody 496 is expected to bind IL-17F at one or more of the following residues:

SER39, MET40, SER41, ARG42, ARG47, ASN53, ARG73, ASN74, LEU75, LYS83, GLU84, ASP85, ILE86, SER87, MET88, ASN89, VAL91, PRO92, GLN94, THR126, PRO127, VAL128.

Example 7

The interaction between 496 and IL-17f was studied by x-ray crystallography.

Crystallisation, Structure Determination and Refinement of the crystal structure of Human IL17f complexed with 496 Fab Crystallisation The human IL17f/496 Fab complex crystallized as pyramids from hanging drops through the vapour phase at 18.5° C. against a reservoir of 500 μl solution containing 0.85M ammonium sulfate, 0.2M sodium potassium tartrate and 0.05M Tris buffer pH 6.9 for 1-2 weeks in Hampton Research VDXm plates. The drops contained 1 μl of protein at 10 mg/ml in 20 mM Hepes pH 7.4, 50 mM NaCl, 0.02% azide, and 1 μl reservoir solution. The crystals belong to the space group H32 with cell dimensions a=b=189.4; c=490.9, and three molecules of the IL17f/496 Fab in the asymmetric unit.

X-ray Diffraction Collection

We collected the x-ray diffraction data through a single IL17f/496 Fab crystal suspended in a litho loop and flash frozen under liquid nitrogen, after briefly passing the crystal through a cryoprotectant solution containing 1.3M ammonium sulphate, 0.2M sodium potassium tartrate and Tris buffer pH 6.9 and 30% glycerol. The diffraction data was collected on an ADSC Quantum 4 charge coupled device at the I03 beamline station at the Diamond synchrotron, Didcot, Oxfordshire, UK. The wavelength of the monochromatic x-ray beam was 0.9796 Å. The reciprocal space was sampled at 1.0° oscillation steps around the $\phi$ goniostat axis. The data were processed with Mosflm (Leslie, A G W, Joint CCP4+ ESF-EAMCB Newsletter on Protein Crystallography, No. 26; CCP4, Collaborative Computational Project, Number 4. Acta Cryst. D50, 760-763 (1994)).

Structure Determination

The crystal structure of human IL17f/496 Fab complex was determined in two steps. First the Fab position was located with the molecular replacement program Phaser (Read, R J, Acta Cryst. D57, 1373-1382 (2001)), using the Fab with the PDB code 1L7I stripped of water molecules. The cross rotation and translation functions were carried out at 4.0 Å resolution and default settings. Three molecules of Fab were located. The searches after translation translation yielded a solution with a high R-factor of after rigid body refinement in CNX (Brunger, A et al, Science, 235, 458-460 (1997)). Although electron density for IL17f was visible in 2 Fo-Fc electron density maps, a molecular replacement solution for IL17f, using IL17f (PDB code 1JPY) was not found. Instead a structure of an IL17a dimer was used to locate this molecule. A solution was found that corresponded to its location along a 2-fold axis. After selecting one half of the IL17a, and overlaying IL17f, a new search model was created that contained one Fab and one half of an IL17f dimer, with resides at the N-terminus removed that caused symmetry clashes. This search model was used to define the final molecular replacement solution for this half-complex.

Model Building and Refinement

The 496 Fab/IL17f structure was built from the rotation and translation operations found by molecular replacement. Using 2 Fo-Fc and Fo-Fc electron density maps, residues in the Fab model were changed to reflect the sequence in the 496 Fab. According to these maps, one can establish the 496 Fab rough model by altering side chain conformations, replacing amino acids present in the model structure by those in the 496 Fab as well as by adding or deleting residues. Adjustments in residue conformer orientations were made for IL17f. We used the interactive computer program O (Jones, T A et al., Acta Cryst. A47, 110-119 (1991)) to perform these manipulations.

This rough model was subjected to rounds of simulated annealing, positional and B-factor refinement using CNX, followed by manual intervention. The refinement and manual rebuilding was monitored by the quality of the 2 Fo-Fc and Fo-Fc electron density maps as well as the value of the crystallographic R and R-free value. The resolution used through the refinement was increased gradually from 4.0 A to 3.2 Å as the refinement proceeded, with a bulk solvent correction used throughout. The model of IL17f/496 Fab complex encompasses residues 15 to 133 of IL17f (see SEQ ID NO. 22), residues 1 to 214 of the light chain of 496 Fab (SEQ ID NO 11) and residues 1 to 227 of the heavy chain of 496 Fab (SEQ ID NO 15). The R-factor of the model is 0.243, and R-free is 0.288 for 56128 reflections. The rms deviation from standard geometry (Engh, R et al., Acta Cryst., A47, 392-400 (1991)) is 0.009 Å for bond lengths and 1.48° for bond angles.

The Epitope

The interaction between 496 and IL-17f (which is a covalent homodimer) studied by x-ray crystallography was of a complex of 496 Fab fragments incubated with human IL-17f. The structure reveals the major contact sites between 496 Fab and IL-17f, and were identified as clustered mainly at the CDR loops of the antibody and along part of the length of IL-17f, interacting with both chains of IL-17f. According to the numbering sequence shown in SEQ ID NO. 22 for the mature IL-17f protein, i.e., the IL-17f protein from which the signal peptide has been cleaved, the residues which interact most closely with the CDR region of 496 Fab within 3.0A, are Gln71, Cys72, Ile86, Asn89, Ser90 and Val128 from the first chain, and Arg47 from the second chain. Major residues of IL-17f that contact 496 Fab within 3.5 A are Gln71, Cys72, Asn74, Leu75, Ile86, Asn89, Ser90, Pro92, Val128, His131 and Gln133 from the first chain, and Arg37, Ser39, Ser41 and Arg47 from the second chain. Residues that contact 496 Fab within 4.0 A are Gln71, Cys72, Arg73, Asn74, Leu75, Ile86, Ser87 Asn89, Ser90, Val91, Pro92, Val128, His131 and Gln133 from the first chain, and Asn33, Gln36, Arg37, Ser39, Ser41, Arg42, Ile44 and Arg47 from the second chain. These residues define the epitope of the 496 antibody.

Lengthy table referenced here

US08679494-20140325-T00001

Please refer to the end of the specification for access instructions.

In further aspect there is provided a crystal structure comprising an epitope as defined herein.

Also provided is a method of generating a three dimensional computer representation employing 10, 20, 30, 40, 50, 60, 70, 80, 90 or 100% of co-ordinates listed in Table 1.

In one embodiment there is provided a machine readable mediume having stored thereon data comprising 10, 20, 30, 40, 50, 60, 70, 80, 90 or 100% of co-ordinates listed in Table 1.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

LENGTHY TABLES

The patent contains a lengthy table section. A copy of the table is available in electronic form from the USPTO web site (http://seqdata.uspto.gov/?pageRequest=docDetail&DocID=US08679494B2). An electronic copy of the table will also be available from the USPTO upon request and payment of the fee set forth in 37 CFR 1.19(b)(3).

We claim:

1. A monoclonal antibody that specifically binds an epitope of human IL-17A, the epitope comprising residues TYR44, ASN45, TRP51, ASN52 and ASP84 of SEQ ID NO: 21 and wherein the monoclonal antibody additionally binds human IL-17F.

2. A chimeric or humanized antibody that specifically binds an epitope of human IL-17A, the epitope comprising residues TYR44, ASN45, TRP51, ASN52 and ASP84 of SEQ ID NO: 21 and wherein the chimeric, or humanized antibody additionally binds human IL-17F.

3. The antibody of claim 2, wherein its binding epitope optionally comprises one or more of the residues selected from the group consisting of SER41, ARG46, HIS54, ARG72, HIS73, HIS86, VAL128, HIS129 and VAL131 of SEQ ID NO: 21.

4. The antibody of claim 2, wherein its binding epitope does not comprise one or more of the amino acid residues selected from the group consisting of ASP80, GLY81 and ASN82 of SEQ ID NO:21.

5. A composition comprising the antibody of claim 2 and a pharmaceutically acceptable excipient.

6. The antibody of any one of claims 2, 3 or 4, which has a binding affinity for human IL-17A of better than 500 pM.

* * * * *